US007383088B2

(12) United States Patent
Spinelli et al.

(10) Patent No.: US 7,383,088 B2
(45) Date of Patent: Jun. 3, 2008

(54) CENTRALIZED MANAGEMENT SYSTEM FOR PROGRAMMABLE MEDICAL DEVICES

(75) Inventors: Julio C. Spinelli, Shoreview, MN (US); Qingsheng Zhu, Little Canada, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 826 days.

(21) Appl. No.: 10/008,354

(22) Filed: Nov. 7, 2001

(65) Prior Publication Data

US 2003/0088290 A1    May 8, 2003

(51) Int. Cl.
A61N 1/362    (2006.01)
(52) U.S. Cl. ...................................... 607/30
(58) Field of Classification Search .............. 607/27, 607/30, 59, 60, 13, 300; 128/925; 705/2, 705/3, 30; 706/45, 924; 600/300
See application file for complete search history.

(56) References Cited

U.S. PATENT DOCUMENTS

| 4,494,950 | A | 1/1985 | Fischell |
| 4,712,179 | A | 12/1987 | Heimer ...................... 364/417 |
| 4,777,960 | A | 10/1988 | Berger et al. |
| 4,809,697 | A | 3/1989 | Causey, III et al. ... 128/419 PT |
| 4,825,869 | A | 5/1989 | Sasmor et al. ......... 128/419 PT |
| 4,886,064 | A | 12/1989 | Strandberg |
| 4,928,688 | A | 5/1990 | Mower ................. 128/419 PG |
| 4,967,749 | A | 11/1990 | Cohen |
| 4,987,897 | A | 1/1991 | Funke |
| 5,031,629 | A | 7/1991 | DeMarzo |
| 5,047,930 | A | 9/1991 | Martens et al. |
| 5,097,831 | A | 3/1992 | Lekholm ................. 128/419 D |
| 5,113,869 | A | 5/1992 | Nappholz et al. ........... 128/696 |

(Continued)

FOREIGN PATENT DOCUMENTS

EP    297675 A1    1/1989

(Continued)

OTHER PUBLICATIONS

Ji, J., "An Ultraminiature CMOS Pressure Sensor for a Multiplexed Cardiovascular Catheter", *IEEE Transactions on Electron Devices*, vol. 39, No. 10, (Oct. 1992), pp. 2260-2264 and pp. 2266-2267.

(Continued)

*Primary Examiner*—George R. Evanisko
(74) *Attorney, Agent, or Firm*—Schwegman, Lundberg & Woessner, P.A.

(57) ABSTRACT

A centralized management system for medical devices includes a network, a central server coupled to the network, and a medical device programmer coupled to the network. The central server includes at least one prescription system for prescribing at least one programmable parameter of a medical device based on at least one characteristic of a patient. The medical device programmer communicates at least one characteristic of a patient to the central server via the network, receives at least one parameter from the central server via the network, and programs the medical device using the at least one parameter. In one embodiment, the central server hosts expert prescription systems defined by multiple experts, and a user selects one of the expert prescription systems. In another embodiment, the central server hosts a custom prescription system defined by the user.

47 Claims, 9 Drawing Sheets

U.S. PATENT DOCUMENTS

| | | | |
|---|---|---|---|
| 5,174,289 A | 12/1992 | Cohen | 128/419 PG |
| 5,226,413 A | 7/1993 | Bennett et al. | 128/419 PG |
| 5,251,626 A | 10/1993 | Nickolls et al. | 607/14 |
| 5,262,944 A | 11/1993 | Weisner et al. | |
| 5,267,560 A | 12/1993 | Cohen | |
| 5,282,838 A | 2/1994 | Hauser et al. | 607/9 |
| 5,292,341 A | 3/1994 | Snell | 607/30 |
| 5,309,919 A | 5/1994 | Snell et al. | |
| 5,311,873 A | 5/1994 | Savard et al. | |
| 5,321,618 A | 6/1994 | Gessman | 364/413.06 |
| 5,372,607 A | 12/1994 | Stone et al. | 607/30 |
| 5,421,830 A | 6/1995 | Epstein et al. | 607/30 |
| 5,431,691 A * | 7/1995 | Snell et al. | 607/27 |
| 5,441,047 A | 8/1995 | David et al. | |
| 5,456,952 A | 10/1995 | Garza et al. | 427/489 |
| 5,507,782 A | 4/1996 | Kieval et al. | |
| 5,540,727 A | 7/1996 | Tockman et al. | 607/18 |
| 5,549,654 A | 8/1996 | Powell | 607/32 |
| 5,576,952 A | 11/1996 | Stutman et al. | |
| 5,594,638 A * | 1/1997 | Iliff | 705/3 |
| 5,607,460 A * | 3/1997 | Kroll et al. | 607/30 |
| 5,613,495 A | 3/1997 | Mills et al. | |
| 5,626,630 A | 5/1997 | Markowitz et al. | |
| 5,630,835 A | 5/1997 | Brownlee | 607/60 |
| 5,666,487 A | 9/1997 | Goodman et al. | |
| 5,690,690 A | 11/1997 | Nappholz et al. | 607/30 |
| 5,693,076 A * | 12/1997 | Kaemmerer | 607/59 |
| 5,697,959 A | 12/1997 | Poore | |
| 5,716,382 A | 2/1998 | Snell | 607/30 |
| 5,720,771 A | 2/1998 | Snell | 607/60 |
| 5,722,999 A | 3/1998 | Snell | 607/32 |
| 5,724,985 A | 3/1998 | Snell et al. | 128/697 |
| 5,731,296 A | 3/1998 | Sollevi | |
| 5,752,976 A * | 5/1998 | Duffin et al. | 607/32 |
| 5,759,199 A | 6/1998 | Snell et al. | 607/60 |
| 5,792,203 A | 8/1998 | Schroeppel | |
| 5,800,473 A * | 9/1998 | Faisandier | 607/59 |
| 5,833,623 A | 11/1998 | Mann et al. | 600/523 |
| 5,860,918 A | 1/1999 | Schradi et al. | 600/300 |
| 5,891,178 A | 4/1999 | Mann et al. | 607/27 |
| 5,911,132 A * | 6/1999 | Sloane | 705/3 |
| 5,935,078 A | 8/1999 | Feierbach | |
| 5,935,081 A | 8/1999 | Kadhiresan | |
| 5,987,519 A | 11/1999 | Peifer et al. | |
| 6,001,060 A | 12/1999 | Churchill et al. | |
| 6,015,388 A | 1/2000 | Sackner et al. | |
| 6,016,442 A | 1/2000 | Hsu et al. | 600/518 |
| 6,016,447 A | 1/2000 | Juran et al. | |
| 6,045,513 A | 4/2000 | Stone et al. | |
| 6,070,101 A | 5/2000 | Struble et al. | 607/9 |
| 6,076,015 A | 6/2000 | Hartley et al. | |
| 6,091,990 A | 7/2000 | Hsu et al. | 607/5 |
| 6,093,146 A | 7/2000 | Filangeri | |
| 6,102,874 A | 8/2000 | Stone et al. | |
| 6,112,224 A | 8/2000 | Peifer et al. | |
| 6,141,586 A | 10/2000 | Mower | |
| 6,148,234 A | 11/2000 | Struble | |
| 6,168,563 B1 | 1/2001 | Brown | 600/301 |
| 6,190,324 B1 | 2/2001 | Kieval et al. | 600/483 |
| 6,240,317 B1 | 5/2001 | Villaseca et al. | 607/60 |
| 6,249,705 B1 * | 6/2001 | Snell | 607/59 |
| 6,250,309 B1 | 6/2001 | Krichen et al. | |
| 6,272,377 B1 | 8/2001 | Sweeney et al. | |
| 6,275,727 B1 | 8/2001 | Hopper et al. | 600/513 |
| 6,280,389 B1 | 8/2001 | Ding et al. | |
| 6,280,409 B1 | 8/2001 | Stone et al. | 604/67 |
| 6,285,907 B1 | 9/2001 | Kramer et al. | |
| 6,304,773 B1 | 10/2001 | Taylor et al. | 600/515 |
| 6,336,900 B1 | 1/2002 | Alleckson et al. | |
| 6,336,903 B1 | 1/2002 | Bardy | 600/508 |
| 6,351,675 B1 | 2/2002 | Tholen et al. | 607/59 |
| 6,363,282 B1 * | 3/2002 | Nichols et al. | 607/30 |
| 6,368,284 B1 | 4/2002 | Bardy | 600/508 |
| 6,370,427 B1 | 4/2002 | Alt et al. | |
| 6,383,136 B1 | 5/2002 | Jordan | 600/300 |
| 6,398,728 B1 | 6/2002 | Bardy | 600/300 |
| 6,400,982 B2 | 6/2002 | Sweeney et al. | |
| 6,411,840 B1 | 6/2002 | Bardy | 600/513 |
| 6,411,847 B1 | 6/2002 | Mower | 607/9 |
| 6,438,407 B1 | 8/2002 | Ousdigian et al. | 600/510 |
| 6,438,408 B1 | 8/2002 | Mulligan et al. | |
| 6,440,066 B1 | 8/2002 | Bardy | 600/300 |
| 6,441,747 B1 | 8/2002 | Khair et al. | |
| 6,442,432 B2 * | 8/2002 | Lee | 607/59 |
| 6,442,433 B1 | 8/2002 | Linberg | 607/60 |
| 6,443,890 B1 | 9/2002 | Schulze et al. | |
| 6,453,201 B1 | 9/2002 | Daum et al. | |
| 6,480,745 B2 | 11/2002 | Nelson et al. | |
| 6,497,655 B1 | 12/2002 | Linberg et al. | |
| 6,526,313 B2 | 2/2003 | Sweeney et al. | |
| 6,542,775 B2 | 4/2003 | Ding et al. | |
| RE38,119 E | 5/2003 | Mower | 607/9 |
| 6,564,104 B2 * | 5/2003 | Nelson et al. | 607/60 |
| 6,564,105 B2 | 5/2003 | Starkweather et al. | |
| 6,585,644 B2 | 7/2003 | Lebel et al. | |
| 6,622,040 B2 | 9/2003 | Ding et al. | |
| 6,622,045 B2 | 9/2003 | Snell et al. | |
| 6,648,823 B2 | 11/2003 | Thompson et al. | |
| 6,650,939 B2 | 11/2003 | Taepke, II et al. | |
| 6,650,944 B2 | 11/2003 | Goedeke et al. | |
| 6,665,558 B2 | 12/2003 | Kalgren et al. | |
| 6,668,194 B2 | 12/2003 | VanHout | |
| 6,669,631 B2 * | 12/2003 | Norris et al. | 600/300 |
| 6,684,103 B2 | 1/2004 | Ding et al. | |
| 6,687,547 B2 * | 2/2004 | Goedeke et al. | 607/60 |
| 6,735,479 B2 | 5/2004 | Fabian et al. | |
| 6,738,667 B2 | 5/2004 | Deno et al. | |
| 6,738,671 B2 | 5/2004 | Christophersom et al. | |
| 6,804,558 B2 * | 10/2004 | Haller et al. | 607/30 |
| 6,811,537 B2 | 11/2004 | Bardy | |
| 6,878,112 B2 | 4/2005 | Linberg et al. | |
| 6,961,617 B1 | 11/2005 | Snell | |
| 7,043,305 B2 | 5/2006 | Kenknight et al. | |
| 7,070,562 B2 * | 7/2006 | Bardy | 600/300 |
| 7,136,707 B2 | 11/2006 | Hall et al. | |
| 7,181,285 B2 | 2/2007 | Lindh et al. | |
| 2001/0007053 A1 | 7/2001 | Bardy | 600/300 |
| 2001/0012955 A1 | 8/2001 | Goedeke et al. | |
| 2001/0031997 A1* | 10/2001 | Lee | 607/59 |
| 2001/0031998 A1 | 10/2001 | Nelson et al. | |
| 2001/0039375 A1 | 11/2001 | Lee et al. | |
| 2001/0039503 A1 | 11/2001 | Chan et al. | |
| 2001/0047125 A1 | 11/2001 | Quy | |
| 2001/0049544 A1 | 12/2001 | Lee | |
| 2002/0013613 A1* | 1/2002 | Haller et al. | 607/60 |
| 2002/0016550 A1 | 2/2002 | Sweeney et al. | 600/515 |
| 2002/0019586 A1 | 2/2002 | Teller et al. | |
| 2002/0023654 A1 | 2/2002 | Webb | |
| 2002/0026103 A1 | 2/2002 | Norris et al. | |
| 2002/0026223 A1 | 2/2002 | Riff et al. | 607/27 |
| 2002/0049482 A1 | 4/2002 | Fabian et al. | |
| 2002/0052539 A1 | 5/2002 | Haller et al. | |
| 2002/0082868 A1 | 6/2002 | Pories et al. | |
| 2002/0115939 A1 | 8/2002 | Mulligan et al. | |
| 2002/0120311 A1 | 8/2002 | Lindh et al. | |
| 2002/0123672 A1 | 9/2002 | Christophersom et al. | 600/300 |
| 2002/0138012 A1 | 9/2002 | Hodges et al. | |
| 2002/0193667 A1 | 12/2002 | McNair | |
| 2003/0050803 A1 | 3/2003 | Marchosky | |
| 2003/0074029 A1 | 4/2003 | Deno et al. | |
| 2003/0088290 A1 | 5/2003 | Spinelli et al. | |
| 2003/0144702 A1 | 7/2003 | Yu et al. | |
| 2003/0144703 A1 | 7/2003 | Yu et al. | |
| 2003/0144711 A1 | 7/2003 | Pless et al. | |

| | | |
|---|---|---|
| 2003/0171791 A1 | 9/2003 | KenKnight et al. |
| 2004/0117204 A1 | 6/2004 | Mazar et al. |
| 2004/0122294 A1 | 6/2004 | Hatlestad et al. |
| 2004/0122295 A1 | 6/2004 | Hatlestad et al. |
| 2004/0122296 A1 | 6/2004 | Hatlestad et al. |
| 2004/0122297 A1 | 6/2004 | Stahmann et al. |
| 2004/0122484 A1 | 6/2004 | Haltestad et al. |
| 2004/0122485 A1 | 6/2004 | Stahmann et al. |
| 2004/0122486 A1 | 6/2004 | Stahmann et al. |
| 2004/0122487 A1 | 6/2004 | Haltestad et al. |
| 2004/0133080 A1 | 7/2004 | Mazar |
| 2004/0133246 A1 | 7/2004 | Ding et al. |
| 2004/0143304 A1 | 7/2004 | Hall et al. |
| 2004/0230456 A1 | 11/2004 | Lozier et al. |
| 2006/0195163 A1 | 8/2006 | KenKnight et al. |

FOREIGN PATENT DOCUMENTS

| | | |
|---|---|---|
| EP | 709058 A1 | 5/1996 |
| EP | 10066698 A2 | 1/2001 |
| WO | WO-9914882 A2 | 3/1999 |
| WO | WO-00/41765 | 7/2000 |
| WO | WO-00/41766 | 7/2000 |
| WO | WO-01/03575 | 1/2001 |
| WO | WO-01/24876 A1 | 4/2001 |
| WO | WO-0167948 A2 | 9/2001 |
| WO | WO-2004104901 A1 | 12/2004 |

OTHER PUBLICATIONS

Barbaro, V., et al., "A portable unit for remote monitoring of pacemaker patients", *Journal of Telemedicing and Telecare*, vol. 3, No. 2, (1997),96-102.

Bourge, Robert, et al., "Noninvasive Rejection Monitoring of Cardiac Transplants Using High Resolution Intramyocardial Electrograms", *PACE*, vol. 21, Part II, (Nov. 1998),2338-2344.

Girouard, Steven D., et al., "Cardiac Rhythm Management Systems and Methods Predicting Congestive Heart Failure Status", Application Filed: Aug. 6, 2002 U.S. Appl. No. 10/213,268, 33 pgs.

Hatlestad, John, "Methods and Devices for Detection of Context When Addressing a Medical Condition of a Patient", Application Filed: Oct. 11, 2002 U.S. Appl. No. 10/269,611, CPI Reference No. 01-173,29 pages.

Hutten, H., et al., "Cardiac pacemaker as bridge to cardiac telemonitoring", *Biomedizinische Technik*, 41(6), *Institut for Elektro-und Biomedizinische Technik Technische Universitat Graz. English Abstract*, (Jun. 1996),158-165.

Hutten, H., et al., "Cardiac Telemonitoring through the Linkage of Close-up Telemetry and Internet Transmission", *Institute for Electro-and Biomedical Technology, Technical University of Graz Inffeldgasse, 42 English Abstract*, (1997),67-69.

Kenknight, Bruce H., et al., "Method and Apparatus for Establishing Context Among Events and Optimizing Implanted Medical Device Performance", Date Filed: Mar. 6, 2002 U.S. Appl. No. 10/093,353, 43 pgs.

Mower, Morton, U.S. Patent Office Patent Application Information Retrieval (PAIR) search results for U.S. Appl. No. 10/214,474, filed Aug. 8, 2002, entitled *"Method and Apparatus for Treating Hemodynamic Disfunction"*, 3.

Smith, R.A., et al., "An intranet database for pacemaker patients", *International Journal of Medical Informatics*, 47, (1997),79-82.

Zhu, Qingsheng, et al., "Method and Apparatus for Determining Changes in Heart Failure Status", Application Filed: Nov. 15, 2001 U.S. Appl. No. 10/001,223, 22 pgs.

Hall, Jeffrey A., et al., "Recordable Macros for Pacemaker Follow-Up", U.S. Appl. No. 10/348,191, filed Jan. 21, 2003, 17 pgs.

Lercher, P., "The Impact of the Multicenter Automatic Defibrillator Implantation Trial II in a University Hospital; Do all Patients with Myocardial Infarction and Reduced Left Ventricular Function need an Implantable Cardioverter-Defibrillator?", *Wiener Klinische Wochenschrift*, 1115, Abstract in English,(Mar. 31, 2003),167-174.

Lozier, Luke R., et al., "System for Identifying Candidates for ICD Implantation", U.S. Appl. No. 10/438,261, filed May 14, 2003, 15 pgs.

Moss, A. J., "MADIT-II: Substudies and Their Implications", *Cardiac Electrophysiology Review*, 7, (Dec. 2003),430-433.

Moss, A. J., "Prophylactic Implantation of a Defibrillator in Patients with Myocardial Infarction and Reduced Ejection Fraction", *The New England Journal of Medicine*, 346, (Mar. 21, 2002),877-883.

Nelson, Chester G., et al., "Dynamic Bandwidth Monitor and Adjuster for Remote Communications with a Medical Device", U.S. Appl. No. 60/173,083, filed Dec. 24, 1999, 12 pgs.

Kenknight, Bruce H., "Method and Apparatus for Establishing Context Among Events and Optimizing Implanted Medical Device Performance", U.S. Appl. No. 11/381,051, filed May 1, 2006, 44 Pages.

"U.S. Appl. No. 09/748,791 Advisory Action mailed Aug. 4, 2004", 3 pgs.

"U.S. Appl. No. 09/748,791 Final Office Action mailed Mar. 9, 2004", 6 pgs.

"U.S. Appl. No. 09/748,791 Final Office Action mailed Aug. 23, 2005", 6 pgs.

"U.S. Appl. No. 09/748,791 Non Final Office Action mailed Feb. 3, 2005", 8 pgs.

"U.S. Appl. No. 09/748,791 Non Final Office Action mailed Feb. 10, 2006", 11 pgs.

"U.S. Appl. No. 09/748,791 Non Final Office Action mailed Feb. 21, 2003", 9 pgs.

"U.S. Appl. No. 09/748,791 Non Final Office Action mailed Aug. 28, 2002", 9 pgs.

"U.S. Appl. No. 09/748,791 Non Final Office Action mailed Sep. 17, 2003", 8 pgs.

"U.S. Appl. No. 09/748,791 Preliminary Amendment filed Feb. 21, 2001", 2 pgs.

"U.S. Appl. No. 09/748,791 Response filed May 10, 2006 to Non Final Office Action mailed Feb. 10, 2006", 8 pgs.

"U.S. Appl. No. 09/748,791 Response filed Jul. 5, 2005 to Non Final Office Action mailed Feb. 3, 2005", 7 pgs.

"U.S. Appl. No. 09/748,791 Response filed Jul. 9, 2004 to Final Office Action mailed Mar. 9, 2004", 11 pgs.

"U.S. Appl. No. 09/748,791 Responce filed Jul. 21, 2003 to Non Final Office Action mailed Feb. 21, 2003", 12 pgs.

"U.S. Appl. No. 09/748,791 Response filed Nov. 23, 2005 to Final Office Action mailed Aug. 23, 2005", 7 pgs.

"U.S. Appl. No. 09/748,791 Response filed Nov. 25, 2002 to Non Final Office Action mailed Aug. 28, 2002", 7 pgs.

"U.S. Appl. No. 09/748,791 Response filed Dec. 17,2003 to Non Final Office Action mailed Sep. 17, 2003", 10 pgs.

US 6,527,714, 03/2003, Bardy (withdrawn)

* cited by examiner

CENTRALIZED MANAGEMENT SYSTEM FOR PROGRAMMABLE MEDICAL DEVICES

FIELD OF THE INVENTION

The present invention relates to the field of programmable medical devices. More particularly, this invention relates to a management system for medical devices that have at least one parameter that is programmable based upon at least one characteristic of a patient.

BACKGROUND OF THE INVENTION

Implantable medical devices are commonly used for treating various medical conditions, many of which relate to the heart. For example, cardiac rhythm management (CRM) implantable devices are often implanted in patients to deliver therapy to the heart.

CRM implantable devices include, for example, cardiac pacemakers or "pacers". Pacers deliver timed sequences of low energy electrical stimuli, called "pace pulses", to the heart via an intra vascular leadwire or catheter (referred to as a "lead") having one or more electrodes disposed in or about the heart. The pace pulses initiate heart contractions in a process called "capturing" the heart. By properly timing the delivery of the pace pulses, a heart with an irregular cardiac rhythm (i.e., a cardiac arrhythmia) can be induced to contract with a proper rhythm, thereby improving its efficiency as a pump. Pacers are often used to treat patients with bradyarrhythmias (i.e., hearts that beat too slowly, or beat irregularly).

CRM implantable devices also include cardioverters or defibrillators that are capable of delivering higher energy electrical stimuli to the heart. Defibrillators are often used to treat patients with tachyarrhythmias (i.e., hearts that beat too quickly). Such too-fast heart rhythms can cause the heart to pump inefficiently since the heart is not allowed sufficient time to fill with blood before contracting to expel the blood. A defibrillator is capable of delivering a high energy electrical stimulus that is sometimes referred to as a "defibrillation countershock". The countershock interrupts the tachyarrhythmia to allow the heart to re-establish a normal rhythm for efficiently pumping the blood. Still other types of CRM implantable devices include, for example, pacer/defibrillators that combine the functions of both pacers and defibrillators, drug delivery devices, or any other implantable medical devices that are used for diagnosing and/or treating cardiac arrhythmias.

CRM implantable devices are often capable of delivering therapy to the heart of a patient in a manner that depends on one or more parameters that can be set or adjusted by the patient's physician. For example, a pacer may have programmable parameters such as atrioventricular (AV) delay (i.e., the length of time between an atrial sensed or atrial paced event and the delivery of a ventricular output pulse), an LV offset (i.e., the length of time between a sensed or paced event in a first ventricle and the delivery of an output pulse to a second ventricle), a target heart rate, whether or not to turn on rate smoothing, smoothing percentage for increasing rate, smoothing percentage for decreasing rate, etc. The programmable parameters depend on the particular CRM implantable device, and are typically intended to be programmed based upon the physician's evaluation of the patient.

The primary clinical tool that allows a physician to set or update programmable parameters of a CRM implantable device is a medical device programmer. Such medical device programmers often use inductive coils to provide bidirectional telemetry between the programmer and the implantable device. By using such a programmer, a physician can receive and view stored cardiac and system data from the implantable device, and can send programming instructions back down to the implantable device. Thus, programmers allow physicians to set or adjust the programmable parameters of implantable medical devices.

As additional therapeutic features are introduced into CRM implantable devices, programming such devices to provide optimal therapy for a particular patient has become an increasingly complicated task for medical practitioners. For example, many medical practitioners who may implant only a few devices per year do not have the time nor the resources that would be needed to optimally program such devices. Even practitioners more familiar with such devices, such as physicians who perform perhaps 50 implants per year and who may know how to create custom profiles for particular classes of patients for particular devices, typically do not have the time nor the resources to stay current with each new development in the field. Such problems are likely to worsen as the number of different types of implantable devices increases, and as each type of implantable device becomes more complex. As a result of such problems, many if not most practitioners use only the factory-set, default parameters of CRM implantable devices, while other medical practitioners may adjust only a subset of the parameters from the factory-set parameters. While using default parameters may provide adequate therapy for a generalized class of patients, the use of such parameters often does not provide optimal therapy for a particular patient.

Thus, even though medical device programmers give medical practitioners the capability to set or update the programmable parameters of CRM implantable devices, the medical practitioners often lack the resources and the knowledge that would be needed to optimally program such devices to provide optimal therapy for particular patients. This problem is likely to worsen as new types of CRM implantable devices are developed, and as new and additional features are added to new and existing CRM implantable devices. As a result, the therapeutic benefits of such devices may not reach their full potential.

Therefore, it would be advantageous to provide an improved system and method for programming CRM implantable medical devices that solves these and other problems.

SUMMARY OF THE INVENTION

In accordance with one aspect of the present invention, a centralized management system for medical devices includes a network, a central server coupled to the network, and a medical device programmer also coupled to the network. The central server includes at least one prescription system for prescribing at least one programmable parameter of a medical device based upon at least one characteristic of a patient. The medical device programmer communicates at least one characteristic of a patient to the central server via the network, receives at least one programmable parameter from the central server via the network, and programs the medical device using the at least one programmable parameter.

In accordance with another aspect of the present invention, a central server for use in a centralized management system for medical devices includes a network interface for communicating with a medical device programmer over a network, and at least one prescription system coupled to the network interface. Each prescription system is able to receive at least one characteristic of a patient from the medical device programmer via the network, to prescribe at least one programmable parameter of a medical device based upon the at least one characteristic of the patient, and to transmit the at least one prescribed programmable parameter to the medical device programmer via the network.

In accordance with another aspect of the invention, a medical device programmer for use in a centralized management system for medical devices includes a network interface for communicating with a central server over a network, a medical device interface for communicating with a medical device, and a processor coupled to the network interface and the medical device interface. The processor communicates at least one characteristic of a patient to the central server via the network, receives at least one prescribed parameter of the medical device from the central server via the network, and programs the medical device using the at least one prescribed parameter via the medical device interface.

In accordance with another aspect of the present invention, a method of programming a programmable medical device includes determining at least one characteristic of a patient at a medical device programmer, communicating the at least one characteristic to a central server, determining at least one programmable parameter for a medical device based upon the at least one characteristic using a prescription system hosted by the central server, communicating the at least one programmable parameter to the medical device programmer, and programming the medical device using the at least one programmable parameter.

These and various other features as well as advantages which characterize the present invention will be apparent to a person of ordinary skill in the art upon reading the following detailed description and reviewing the associated drawings.

DESCRIPTION OF THE PREFERRED EMBODIMENTS

Figure 1:
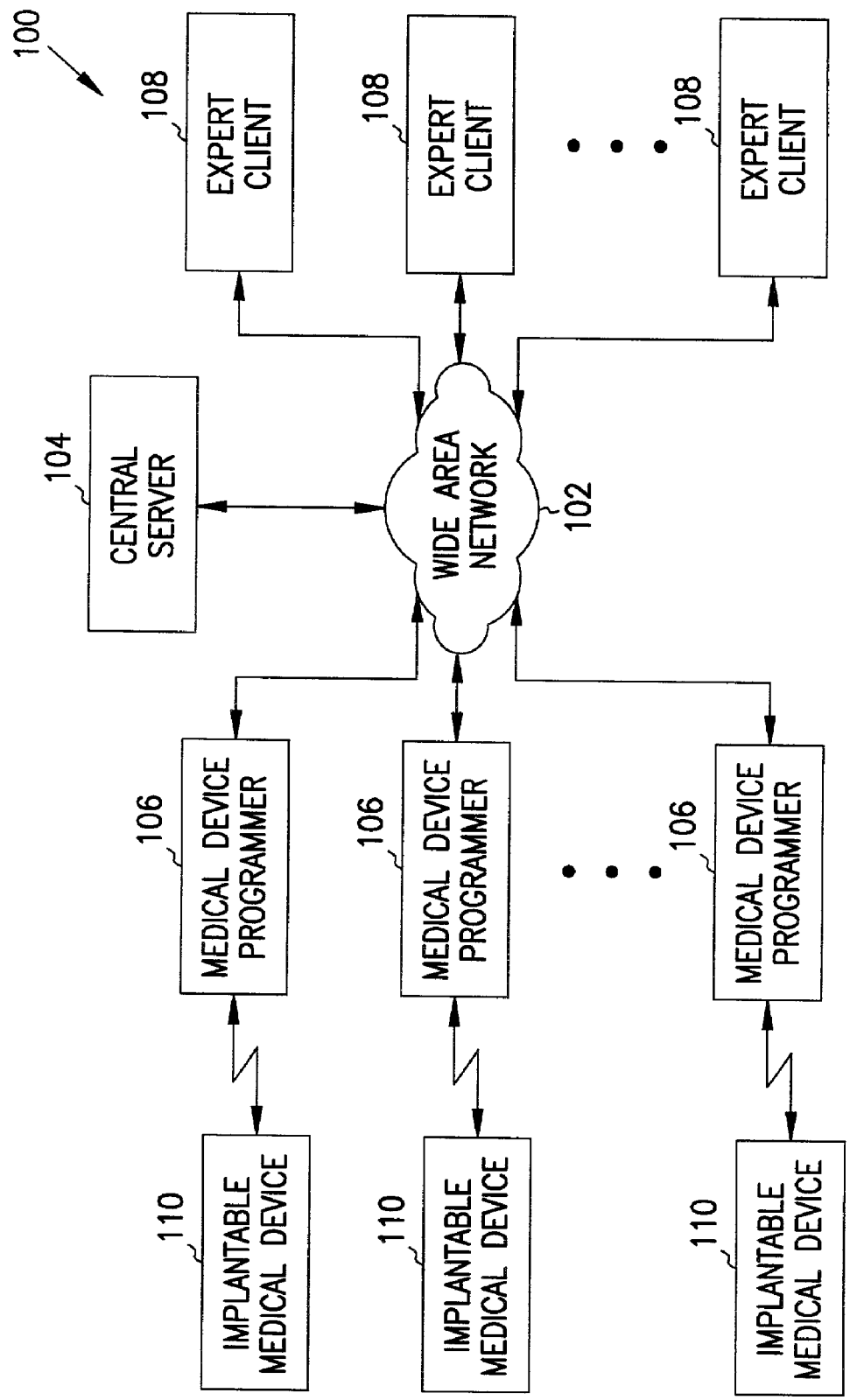
FIG. 1 is a block diagram of a centralized management system for implantable medical devices that have at least one parameter that is programmable based upon at least one characteristic of a patient, in accordance with one embodiment of the invention.

In the following detailed description, reference is made to the accompanying drawings, which form a part hereof, and in which is shown by way of illustration specific embodiments in which the invention may be practiced. In the drawings, like numerals refer to like components throughout the views. These embodiments are described in sufficient detail to enable those skilled in the art to practice the invention, and it is to be understood that the embodiments may be combined, or that other embodiments may be utilized and that structural, logical and electrical changes may be made without departing from the spirit and scope of the invention. The following description is, therefore, not to be taken in a limiting sense, and the scope of the invention is defined by the appended claims and their equivalents.

Referring to FIG. 1, a centralized management system 100 for implantable medical devices is shown, in accordance with one embodiment of the present invention. System 100 includes a network 102, a central server 104 coupled to network 102, one or more medical device programmers 106 coupled to network 102, and one or more expert clients 108 also coupled to network 102. In system 100, each medical device programmer 106 and each expert client 108 is capable of communicating with central server 104 via network 102. In another embodiment of the invention, system 100 does not include any of the expert clients.

In one embodiment, network 102 is a wide area network (WAN) that allows for bidirectional communications to occur over a wide geographic area. For example, network 102 may include point-to-point unswitched private communication lines such as T1 or T3 lines, or switched lines like those of the public switched telephone network (PSTN), ISDN lines, etc. For another example, network 102 includes the Internet. Using a WAN eliminates or reduces any geographic restrictions placed on the locations of central server 104, medical device programmer(s) 106, and expert client(s) 108, and any two of these components can be physically located close to one another, far from one another, or any distance in between. In various embodiments, the communications between central server 104, programmer(s) 106 and expert client(s) 108 takes place over an electrical, optical, radio-frequency (RF), or wireless communication medium, or a combination of such communication mediums.

In another embodiment, network 102 is a local area network (LAN) that allows for communications to occur over a local geographic area, such as within a building or complex. For example, network 102 may include an Ethernet or token ring network in a hospital or hospital complex. In yet another embodiment, network 102 is a metropolitan area network (MAN) generally covering a metropolitan geographic area such as a city, town or county.

Central server 104 hosts at least one prescription system for prescribing at least one programmable parameter of a medical device based on at least one characteristic of a patient. The at least one patient characteristic is received by central server 104 from any of the medical device programmers 106 via network 102, and the at least one prescribed programmable parameter is then transmitted back to that programmer via network 102 for use in programming a medical device that will provide therapy for the patient.

Thus, by executing a prescription system, central server 104 is capable of prescribing one or more programmable parameters for a medical device based upon at least one characteristic of a patient. In one embodiment, central server 104 includes a computer system and software that are dedicated to hosting the at least one prescription system. In another embodiment, central server 104 includes software that executes on a computer system that runs other applications. Central server 104 may thus include a combination of hardware and software, or software only. Central server 104, and its operation in system 100, is described further below.

Each medical device programmer 106 communicates at least one characteristic of a patient to central server 104 via network 102, and receives at least one prescribed programmable parameter of a medical device from central server 104 via network 102. Each medical device programmer 106 receives the at least one characteristic from any or all of a number of different sources (described below), and uses the at least one prescribed parameter to program an implantable medical device 110 coupled to the programmer 106. Each medical device programmer 106, and its operation in system 100, is described further below.

As illustrated in FIG. 1, each medical device programmer 106 allows a medical practitioner (e.g., a physician, nurse, technician, etc.) to program an implantable medical device 110. In one embodiment, each implantable medical device 110 is a cardiac rhythm management (CRM) implantable device such as a pacer, a cardioverter or defibrillator, a pacer/defibrillator, or another type of CRM implantable device such as a drug delivery or another type of implantable medical device used to diagnose or treat cardiac arrhythmias.

In another embodiment, any or all of medical device programmers 106 is coupled to, and is capable of programming, another type of implantable medical device that is programmed according to the individual characteristics of the patient, but is not used to diagnose or treat cardiac arrhythmias. For example, any or all of programmers 106 may be coupled to, and be capable of programming, an implantable drug delivery device that is not used for CRM purposes. In yet another embodiment, any or all of programmers 106 is coupled to, and is capable of programming, a non-implantable medical device that is programmed according to the individual characteristics of the patient. For example, any or all of programmers 106 may be coupled to, and be capable of programming, an external pacer that is disposed on the chest of a patient in order to deliver therapeutic pace pulses.

In one embodiment, centralized management system 100 is capable of programming just one type of medical device. For example, system 100 could be capable of programming only a particular type of pacer. In another embodiment, system 100 can program more than one type of medical device. In this embodiment, any of multiple types of medical devices can be programmed using any of medical device programmers 106. For example, a practitioner equipped with a programmer 106 can use central server 104 to prescribe a first set of programming parameters to program a pacer for a first patient, and a second set of programming parameters to program a defibrillator (or another type of pacer) for a second patient. In one embodiment, programmer 106 identifies the type of medical device being programmed (e.g., from a user input), and transmits that information to the central server.

Note that a CRM or non-CRM implantable medical device is programmable by an appropriate medical device programmer 106 regardless of whether or not that device has actually been implanted into the body of a patient. For example, an implantable pacer can be programmed before that pacer is implanted into the body of a patient, and can also be programmed when that pacer is outside the body (e.g., before being implanted). Thus, an "implantable" medical device refers to a medical device that is capable of being implanted into the body of a patient, regardless of whether or not that device is actually implanted.

In the embodiment of FIG. 1, system 100 includes one or more expert clients 108. Each expert client 108 is used by an expert to define and/or update an expert prescription system that is hosted by central server 104, via network 102. Each expert prescription system is configured by the respective expert to prescribe one or more programmable parameters for a medical device (or different types of medical devices) based on at least one characteristic of a patient, in accordance with the expert's knowledge and skills. In one embodiment, each expert client 108 includes a workstation, personal computer or other computing device that is programmed to perform the functions described herein. In another embodiment, one or more expert clients 108 are hosted by the computer system that serves as central server 104. Each expert client 108, and its operation, is described further below.

In another embodiment, system 100 does not include any expert clients 108. In such an embodiment, information representing each expert's knowledge and skills may be entered directly into central server 104 to define or update the prescription system of that expert. For example, an expert could develop an expert system offline, and that expert system could be loaded onto central server 104 using a magnetic or optical disc, or other medium for data exchange. Alternatively, if central server 104 does not include any expert prescription systems, information representing an expert's knowledge and skills would not be needed.

Thus, FIG. 1 illustrates one embodiment of a centralized management system 100 for implantable medical devices 110, which includes a network 102, a central server 104, one or more medical device programmers 106, and one or more expert clients 108. Central server 104 includes at least one prescription system for prescribing at least one programmable parameter of a medical device based on at least one characteristic of a patient. Each medical device programmer 106 is configured to transmit at least one characteristic of a patient to central server 104 via network 102, to receive at least one programmable parameter from central server 104 via network 102, and to program an implantable medical device 110 using the at least one programmable parameter. The components of centralized management system 100 are now described in further detail. While the following discussion often refers to devices 110 as being implantable medical devices, devices 110 can be any type of medical device that is programmable based on at least one characteristic of a patient.

Figure 2:
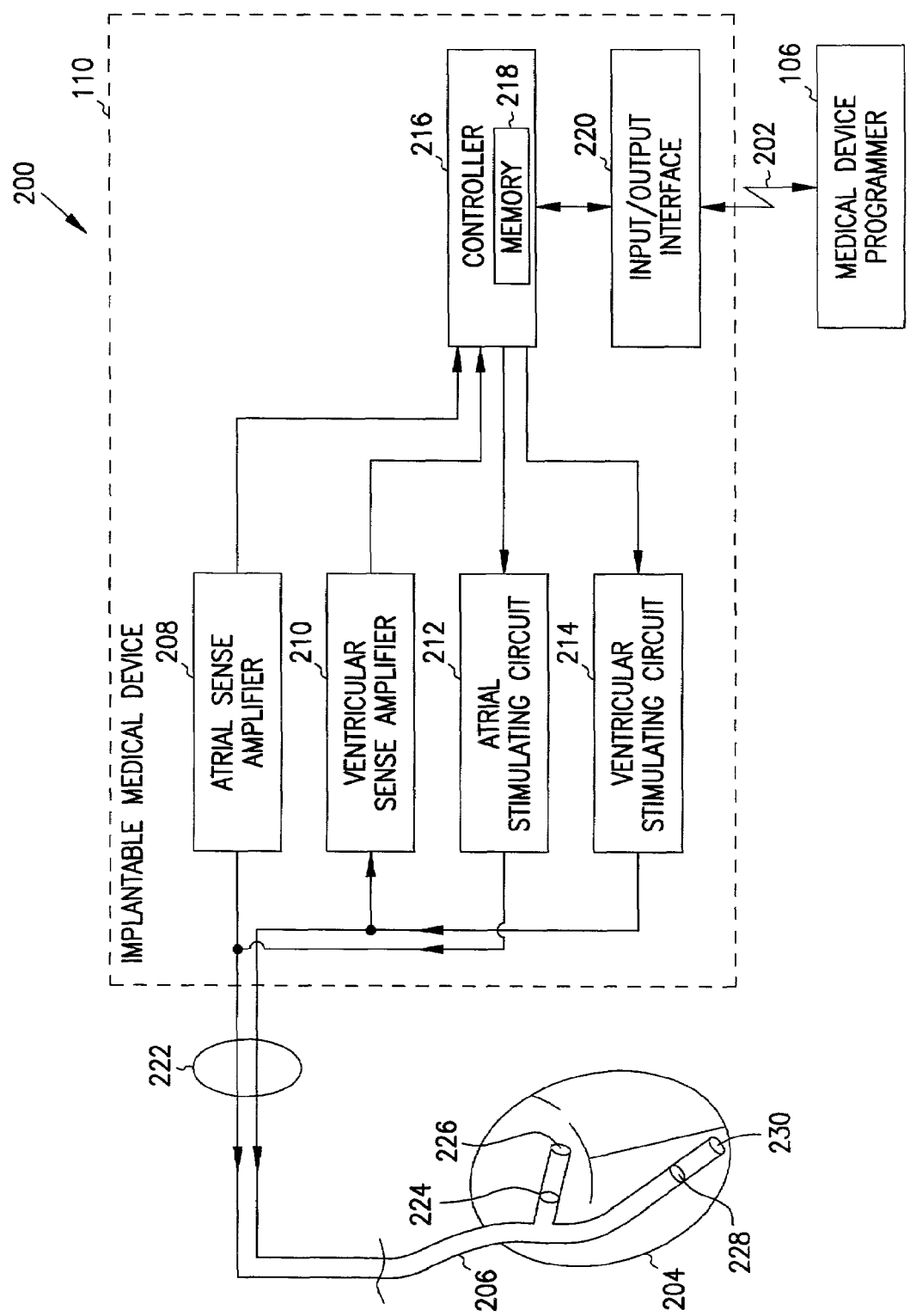
FIG. 2 is a block diagram including one implantable medical device from FIG. 1.

Referring to FIG. 2, a block diagram 200 shows an exemplary implantable medical device 110, in accordance with one embodiment of system 100. Implantable medical device 110 is configured to communicate with one of medical device programmers 106 via a communications link 202. In one embodiment, link 202 uses radio-frequency (RF) signals that can pass through the body of a patient when device 110 is implanted. In another embodiment, link 106 uses optical signals than can pass through the patient's body when device 110 is implanted. Thus, programmer 106 and implantable medical device 110 can communicate regardless of whether or not device 110 is implanted in a patient. These communications support monitoring, diagnostic and programming functions of device 110.

In this embodiment, implantable medical device 110 is a pacer that is operatively coupled to a patient's heart 204 by a pacing lead 206. The components of implantable medical device 110 include, for example, an atrial sense amplifier 208, a ventricular sense amplifier 210, an atrial stimulating circuit 212, a ventricular stimulating circuit 214, a controller 216, a memory 218, and an input/output (I/O) interface 220. Device 110 may also include other components that are known to people of ordinary skill in the art, such as an accelerometer (not shown) for measuring patient activity. The components of implantable medical device 110 are housed within an implantable housing (indicated by the broken lined box in FIG. 1.) that is implanted in the patient's chest cavity (e.g., in the pectoral region).

Atrial sense amplifier 208, ventricular sense amplifier 210, atrial stimulating circuit 212 and ventricular stimulating circuit 214 are operatively coupled to pacing lead 206 via a pair of conductors 222. Pacing lead 206 includes an atrial sensing electrode 224 and atrial stimulating electrode 226 adapted to be disposed in the right atrial chamber of heart 204, and a ventricular sensing electrode 228 and ventricular stimulating electrode 230 adapted to be disposed in the right ventricular chamber of heart 204. Sensed atrial and ventricular electrical signals generated by sensing electrodes 224 and 228 are applied to atrial and ventricular sense amplifiers 208 and 210, respectively. Atrial and ventricular stimulating signals generated by atrial and ventricular stimulating circuits 212 and 214 are applied to atrial and ventricular stimulating electrodes 226 and 230, respectively. Atrial sense amplifier 208, ventricular sense amplifier 210, atrial stimulating circuit 212, and ventricular stimulating circuit 214, are also each operatively coupled to controller 216.

Controller 216 includes a micro-controller or microprocessor which is configured to execute a program stored in a read-only memory (ROM) portion of memory 218, and to read and write data to and from a random access memory (RAM) portion of memory 218. In one embodiment, memory 218 also includes an electrically-erasable programmable read only memory (EEPROM) portion that is used by the micro-controller or microprocessor for storing and retrieving one or more programmable parameters for the medical device. By executing the program stored in memory 218, controller 216 is configured to process the atrial and ventricular electrical signals from atrial and ventricular sense amplifiers 208 and 210, and to provide control signals to atrial and ventricular stimulating circuits 212 and 214. In response, stimulating circuits 212 and 214 provide stimulating pulses to heart 204 via atrial and ventricular stimulating electrodes 226 and 230 at appropriate times. In other embodiments, controller 216 may include other types of control logic elements or circuitry.

Implantable medical device 110 is capable of delivering therapy to the patient in a manner that depends on one or more parameters than can be programmed by the patient's physician or other medical practitioner using medical device programmer 106. For example, in one embodiment, device 110 is a pacer capable of delivering therapy to heart 204 that has one or more programmable parameters such as an atrioventricular (AV) delay, an LV offset, a target heart rate, whether or not to turn on rate smoothing, smoothing percentage for increasing rate, smoothing percentage for decreasing rate, etc. When any of these or other programmable parameters is downloaded to implantable medical device 110 from medical device programmer 106, controller 216 stores the received parameter value(s) in memory 218. Then, during operation of device 110, controller 216 reads the programmable parameters from memory 218, and uses those values to adjust the operations of device 110.

The implantable medical device shown in FIG. 2 is a dual-chamber pacemaker, since pacemaking functions are provided to both atrial and ventricular chambers of the heart. In another embodiment, one or more of the implantable medical devices is another type of pacemaker, such as a single-chamber pacemaker that senses electrical signals and provides stimulating pulses to a single chamber of the heart. In another embodiment, one or more of the implantable medical devices is another type of CRM device, such as a defibrillator, a pacer/defibrillator, a drug delivery device or another implantable medical device used for diagnosing or treating cardiac arrhythmias. In another embodiment, one or more of the implantable medical devices is a non-CRM implantable medical device such as an implantable drug delivery device not used for CRM purposes. In yet another embodiment, any or all of the medical devices programmed by programmer(s) 106 is a non-implantable medical device that is programmed according to the individual characteristics of the patient. In each case, the medical device includes a memory such as memory 218 in which one or more programmable parameters downloaded from programmer 106 is stored for later use.

Figure 3:
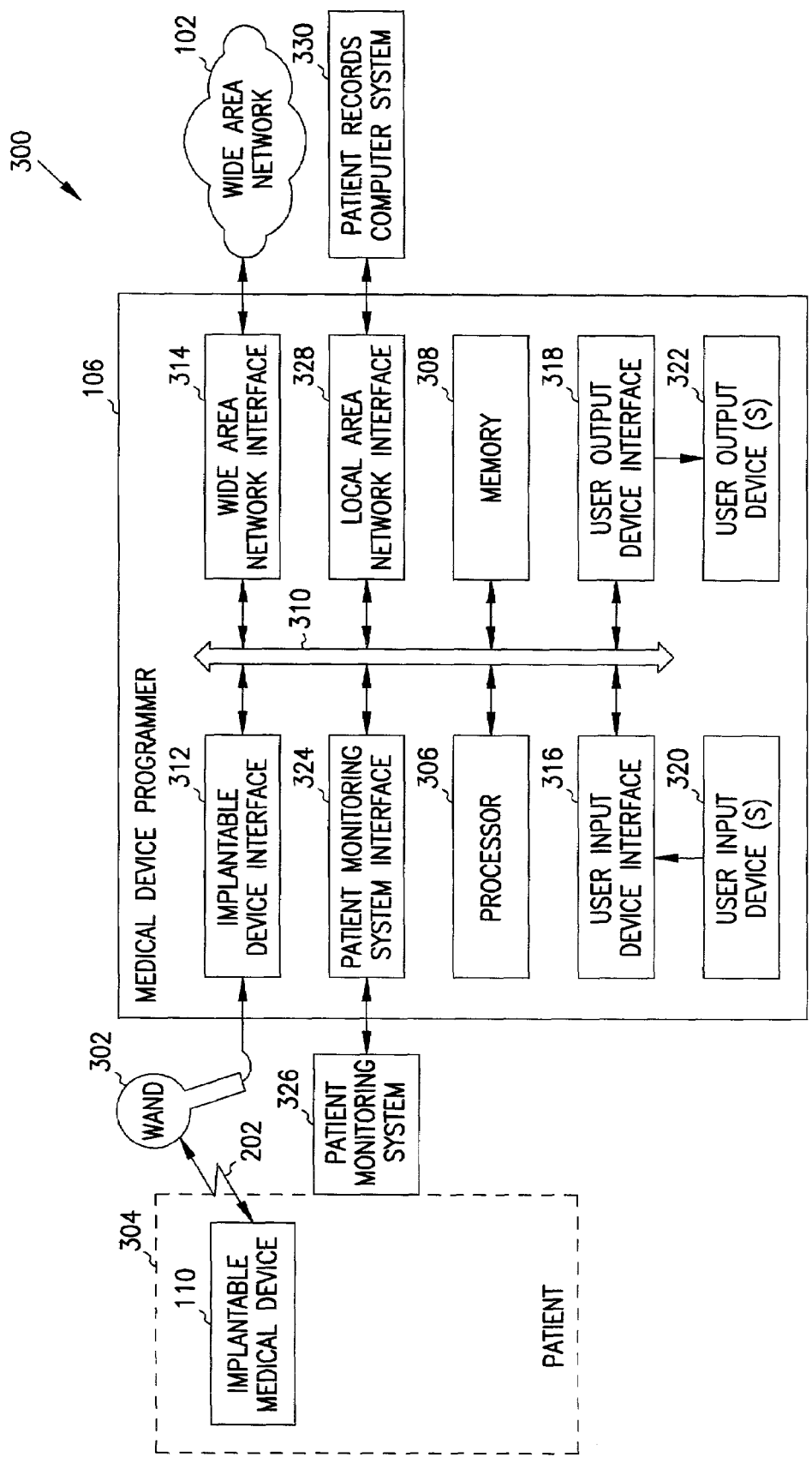
FIG. 3 is a block diagram including one medical device programmer from FIG. 1.

Referring to FIG. 3, a block diagram 300 shows one of medical device programmers 106, in accordance with one embodiment of system 100. Programmer 106 is configured to communicate with one of implantable medical devices 110 via communications link 202. In one embodiment, programmer 106 is electrically coupled to a wand 302 that can be moved into close proximity with a patient 304 to allow RF, optical or a combination of RF and optical signals to pass between wand 302 and a medical device 110 implanted in the patient. Programmer 106 is also configured to communicate with central server 104 via network 102.

In this embodiment, medical device programmer 106 includes a processor 306 and a memory 308 coupled to processor 306 via a communications bus 310. By executing a program stored in memory 308, processor 306 is configured to perform the functions described herein. Programmer 106 also includes an implantable device interface 312, a network interface 314, a user input device interface 316, and a user output device interface 318, each of which is coupled to processor 306 via bus 310. Implantable device interface 312 is coupled to wand 302 to allow processor 306 to communicate with medical device 110. Network interface 314 is coupled to network 102 to allow processor 306 to communicate with central server 104. User input device interface 316 is coupled to one or more user input devices 320 to allow processor 306 to receive inputs from a user (e.g., medical practitioner). User input devices 320 include, for example, one or more of a keyboard, a keypad, a mouse, a touchscreen, a microphone and voice-recognition circuit, a light pen, etc. User output device interface 318 is coupled to one or more user output devices 322 to allow processor 306 to provide outputs to the user. User output devices 322 include, for example, a display, a touchscreen, a printer, a strip-chart recorder, a speaker, etc. In FIG. 3, user input device(s) 320 and user output device(s) 322 are shown as part of programmer 106. Alternatively, any or all of the user input devices and user output devices may be external to programmer 106.

Wand 302, and implantable device interface 312, allow programmer 106 to transmit one or more programmable parameters to implantable medical device 110. In addition, in one embodiment, wand 302 and interface 312 allow programmer 106 to receive signals from implantable medical device 110, such as signals representing one or more characteristics of the patient. For example, these signals could include, or be derived from, signals sensed by sensing electrodes 224 and 228 (FIG. 2), or by some other sensor implanted in the patient.

User input device(s) 320 allow users (e.g., medical practitioners) to input data and/or control operations of programmer 106. For example, where programmer 106 can program more than one type of medical device, a user can actuate an input device 320 to generate an input signal specifying the type of medical device being programmed. For another example, where central server 104 hosts both expert and custom prescription systems, a user can actuate an input device 320 to select between the expert and custom prescription systems. For another example, where central server 104 hosts multiple expert prescription systems, a user can actuate an input device 320 to generate an input signal selecting one of the expert prescription systems. For yet another example, where a user can input one or more patient characteristics, the user can actuate an input device 320 to generate input signals representing at least one characteristic of patient 304. In each case, data representing the input signals is communicated by programmer 106 to central server 104 via network 102 for use by central server 104 in prescribing one or more parameters for the medical device being programmed.

In one embodiment, programmer 106 also includes a patient monitoring system interface 324 that is also coupled to processor 306 via bus 310. Interface 324 is coupled to a patient monitoring system 326 to receive signals that represent at least one characteristic of patient 304. These signals are thus available to processor 306 via bus 310, and are communicated by processor 306 to central server 104 via network 102 for use by central server 104 in prescribing one or more parameters for the medical device being programmed. Patient monitoring system 326 can include, for example, a surface electrocardiograph (ECG) system having one or more sensing electrodes disposed on the patient's chest, or some other type of system for sensing or monitoring one or more characteristics of the patient 304.

In one embodiment, programmer 106 includes an interface 328 to a patient records computer system 330 that is also coupled to processor 306 via bus 310. Patient records computer system 330 stores patient records, such as the medical record of patient 304. Thus, processor 306 may access the medical records of patient 304, and communicate data from this medical record to central server 104 via network 102 for use by central server 104 in prescribing one or more parameters for the medical device being programmed. This data may include, for example, general patient data such as gender, age, etc. of patient 304, or more specific patient data such as the results of a particular diagnostic test. Interface 328 may, for example, include a local area network interface 328 for accessing patient records computer system 330 over a local area network. By providing access to the patient's record, the amount of data that needs to be manually input by the medical practitioner may be decreased. In one embodiment, the medical practitioner enters information identifying the patient into programmer 106 which is used in retrieving the medical record for that patient.

Thus, there are a number of ways by which programmer 106 can gather one or more characteristics of patient 304 for transmittal to central server 104. The ways include having a medical practitioner manually enter data using input device(s) 320, receiving data from implantable medical device 110, receiving data from patient monitoring system 326, and/or receiving data from patient records computer system 330. In any event, the one or more characteristics of patient 304 are communicated to central server 104 via network 102 for use in prescribing one or more parameters for programming the implantable medical device.

In one embodiment, medical device programmer 106 is similar to the ZOOM™ programmer available from the Guidant Corporation of Minnesota, except for the following differences: the addition of interface 314 to central server 104; the (optional) addition of interface 324 to patient monitoring system 326; the (optional) addition of interface 328 to patient records computer system 330; and the configuration (e.g., programming) of medical device programmer 106 to perform the functions described in the present application.

Figure 4:
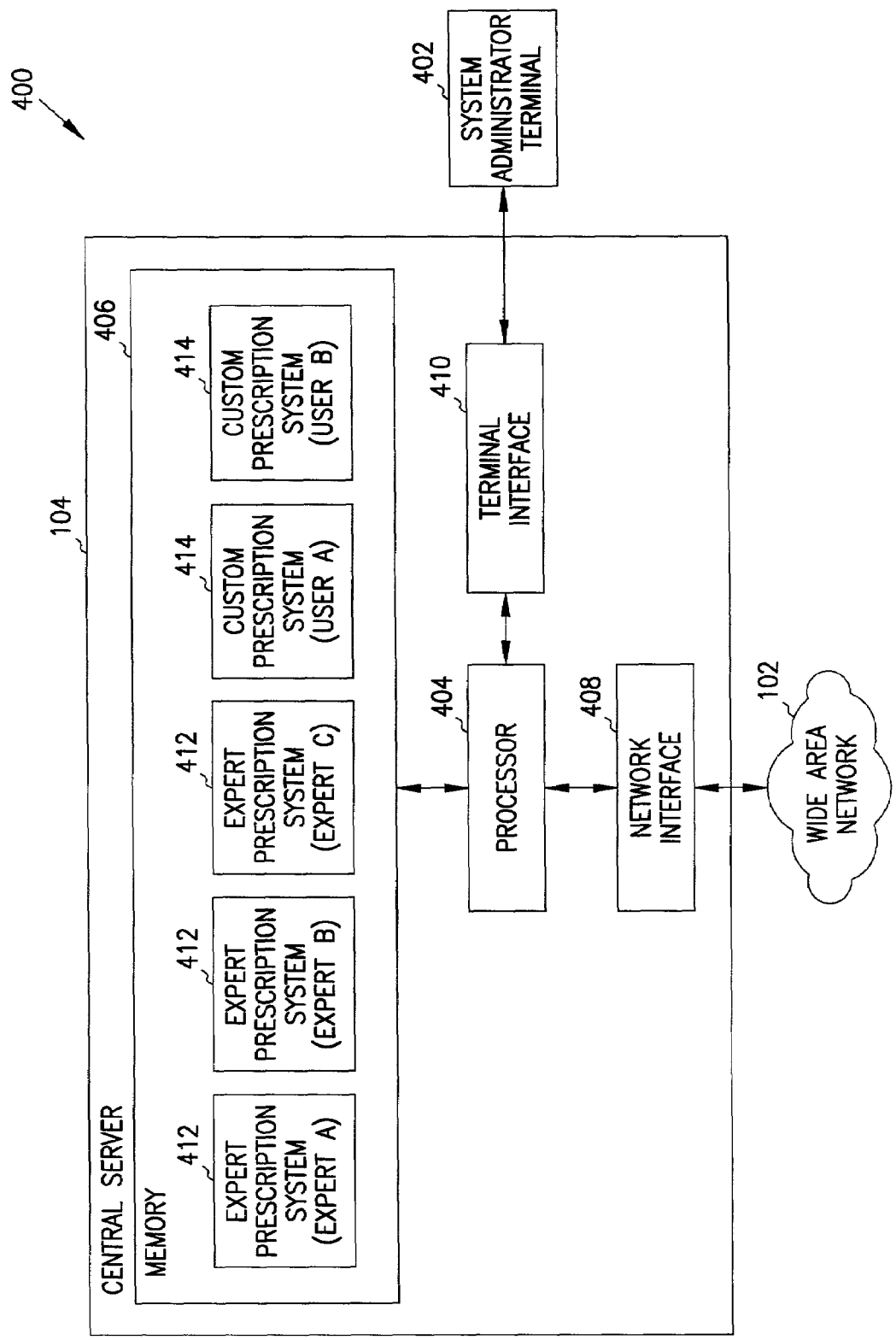
FIG. 4 is a block diagram including the central server from FIG. 1.

Referring to FIG. 4, a block diagram 400 shows central server 104, in accordance with one embodiment of system 100. Central server 104 is configured to communicate with any of medical device programmers 106 or expert clients 108 via network 102. Central server 104 is also configured to communicate with a system administration terminal 402.

In this embodiment, central server 104 includes a processor 404 along with a memory 406, a network interface 408, and a terminal interface 410, each coupled to processor 404. By executing a program stored in memory 406, processor 404 is configured to perform the functions described herein. Network interface 408 is coupled to network 102 to allow processor 404 to communicate with any of programmers 106 or expert clients 108. Terminal interface 410 is coupled to terminal 402 to allow processor 404 to communicate with system administrator terminal 402. In one embodiment, processor 404 is coupled to the other components 406, 408 and 410 of central server 104 via a communications bus (not shown).

Using network interface 408, processor 404 receives one or more characteristics of a patient from one of the medical device programmers 106 in centralized management system 100, and transmits at least one prescribed parameter back to that programmer 106 for use in programming an implantable medical device 110 coupled to that programmer 106. In various embodiments, network interface 408 is also involved in communicating other data between central server 104 and the programmer 106, such as signals input by a user to specify the type of medical device being programmed, to select whether to use an expert or custom prescription system, or to select which of multiple expert prescription systems to use. In one embodiment, using network interface 408, processor 404 also receives data from one or more expert clients 108 which is used for creating or updating one or more expert prescription systems stored in memory 406, in a manner that is further described below.

In the embodiment shown in FIG. 4, central server 104 hosts a number of prescription systems, including a number of expert prescription systems 412. Each expert prescription system 412 comprises an object, including code and data, executed by processor 404 when that expert prescription system is selected. Each expert prescription system 412 is defined by an expert to prescribe at least one parameter of an implantable medical device based on at least one characteristic of a patient. For example, the expert prescription systems 412 shown in FIG. 4 were defined by an Expert A, an Expert B, and an Expert C. Although three expert prescription systems are shown, central server 104 may include fewer than or more than three expert prescription systems, each defined by an expert. As described below, a medical practitioner using a programmer 106 can select one expert prescription system 412 to use in prescribing a set of programmable parameters for the implantable medical device. By selecting such an expert prescription system, the medical practitioner is able to benefit from the knowledge and skills of the expert who defined that expert prescription system.

In the embodiment of FIG. 4, each expert prescription system 412 is defined by a different expert. This embodiment accounts for the fact that the practice of medicine is not standard. In particular, Physician A may provide different advice than Physician B on the same facts, even though both physicians are experts, and the advice of each physician is sound. In one embodiment, information about the experts is stored by central server 104, and is downloaded from central server 104 to programmer 106 for presentation to the user to aid the user in selecting which expert to select. This information may include the expert's name and/or biographical information about the expert, such as information about the expert's education and/or experience. For example, a user could be presented with the choice of selecting between a first expert system that was defined by a Dr. Smith of the Mayo Clinic, or a second expert system that was defined by a Dr. Jones of the Boston Children's Hospital.

In another embodiment, any or all of the expert prescription systems is defined by a group of experts. For example, the manufacturer of a particular implantable medical device could define an expert prescription system for that device that combines the knowledge and skills of a team of experts who were involved in the development of that device. For another example, a team of experts could be assigned the task of working together to define an expert prescription system for a particular medical device. In each case, a medical practitioner using system 100 could then benefit from the combined knowledge and skills of the experts.

In the embodiment shown in FIG. 4, central server 104 also hosts a number of custom prescription systems 414. Each custom prescription system 414 comprises an object, including code and data, executed by processor 404 when that custom system is selected. Each custom prescription system 414 is defined by a user to prescribe at least one parameter of a medical device based on at least one characteristic of a patient. However, unlike expert prescription systems 412, each custom prescription system 414 can only be selected by the user who defined that system 414. For example, FIG. 4 shows two custom prescription systems 414 that were defined by a User A and a User B. In this case, User A can only access the custom prescription system defined by User A, and cannot access the custom prescription system defined by User B. Conversely, User B can only access the custom prescription system defined by User B, and cannot access the custom prescription system defined by User A. A User C cannot access the custom prescription system defined by either User A or User B. To provide this access control, each user is required to logon to system 100 using a login identification. The custom prescription aspects of system 100 are intended for medical practitioners who are familiar enough with implantable medical devices to create custom profiles for particular classes of patients for particular devices, but are not experts in the field who are in a position to give programming advice to other medical practitioners.

As described above, each "user" may be a single medical practitioner. In another embodiment, each "user" may include a group of medical practitioners who are associated with each other. For example, a single "user" may include two physicians who work closely together, and who use centralized management system 100 to share programming data. In this embodiment, the association of the practitioners is used to insure the quality of the custom prescription system. Practitioners not part of the association, however, are not allowed to use the custom prescription system since that system was not created by an expert.

Thus, in one embodiment, central server 104 includes or hosts a number of prescription systems, including one or more expert prescription systems and one or more custom prescription systems, that are selectable by a user to prescribe one or more programming parameters of a medical device based on at least one characteristic of a patient. The manner in which this selection occurs, in one embodiment, is illustrated in FIG. 5.

Figure 5:
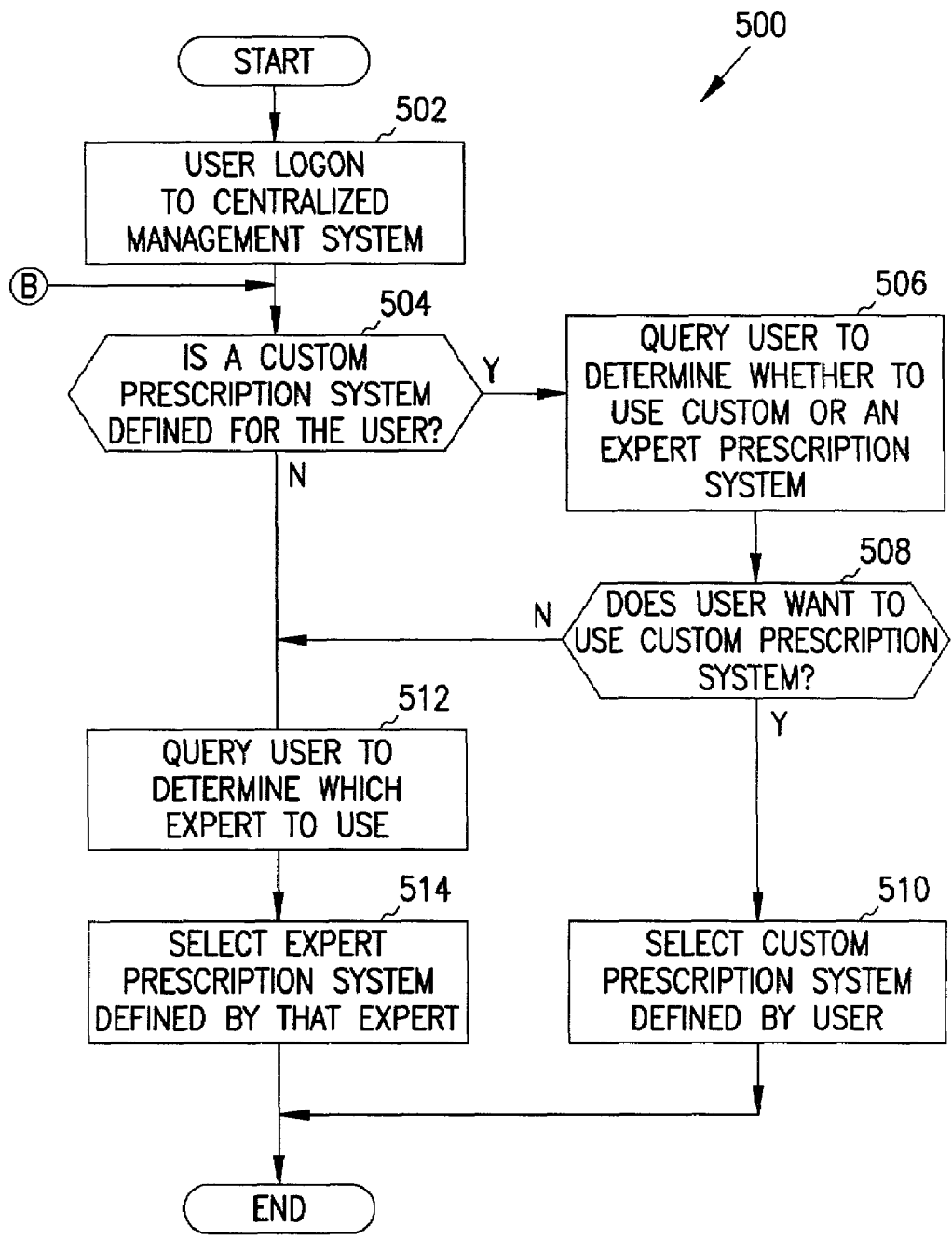
FIG. 5 is a flow chart illustrating prescription system selection logic of the centralized management system of FIG. 1, which allows a user to select a customized prescription system defined by that user, or to select one of a plurality of expert prescription systems.

Referring to FIG. 5, a flow chart 500 illustrates selection logic used by centralized management system 100 to allow a user of a medical device programmer 106 to select one of a plurality of prescription systems hosted by central server 104. At 502, a user logon to system 100 is performed. For example, a user may input his or her user name to programmer 106 using a user input device 320. For additional security, the user may also be requested to input a password. Programmer 106 communicates the user name and password to central server 104, which determines whether the user is authorized. If so, central server 104 sends a message to programmer 106 indicating that the logon was successful, and programmer 106 continues the selection logic. If not, central server 104 sends a message to programmer 106 indicating that the user is not authorized to use system 100. In one embodiment, system 100 presents a message on a user output device 322 to invite the unauthorized user to contact the system administrator to gain access to system 100, if that user is interested in doing so. The system administrator can then use terminal 402 to register the user as an authorized user. Alternatively, the unauthorized user can be allowed to register online to use system 100.

At 504, system 100 determines whether a custom prescription system is defined for the user. For example, if the user is authorized, central server 104 determines whether any of the custom prescription systems 414 stored in memory 406 is defined for that user, and communicates the result to programmer 106. If a custom prescription system 414 is defined for the user, the user is queried at 506 to determine whether to use that custom prescription system, or an expert prescription system. For example, the query is presented to the user using a user output device 322, and the user responds using a user input device 320. Note that the user is not given the choice of using any of the other custom prescription systems since these other systems were not defined by the user, or by an expert. At 508, system 100 determines whether the user wants to use the custom prescription system. If so, then at 510, system 100 selects the custom prescription system defined for that user to prescribe one or more parameters for an implantable medical device 110 being programmed by that user.

At 512, if the user wants to use an expert prescription system, or if a custom prescription system is not defined for the user, then system 100 queries the user to determine which expert to use. For example, central server 104 determines which expert prescription systems 412 are defined for the implantable medical device 110 being programmed, and communicates information about the respective experts to programmer 106 for presentation to the user using a user output device 322. The user selects which of the experts to use using a user input device 320. At 514, system 100 selects the expert prescription system based on the user's input. Thus, system 100 allows a user to select a custom prescription system defined for the user (if any), or to select one expert prescription system from a plurality of expert prescription systems. Central server 104 then uses the selected prescription system to prescribe the one or more parameters of the implantable medical device being programmed.

In another embodiment, central server 104 hosts a number of expert prescription systems, but does not host any custom prescription systems. In this embodiment, flow chart 500 is modified to eliminate 504,506,508 and 510. In another embodiment, central server 104 hosts a number of custom prescription systems, but does not host any expert prescription systems. In this embodiment, flow chart 500 is modified to eliminate 506, 512 and 514.

Figure 6:
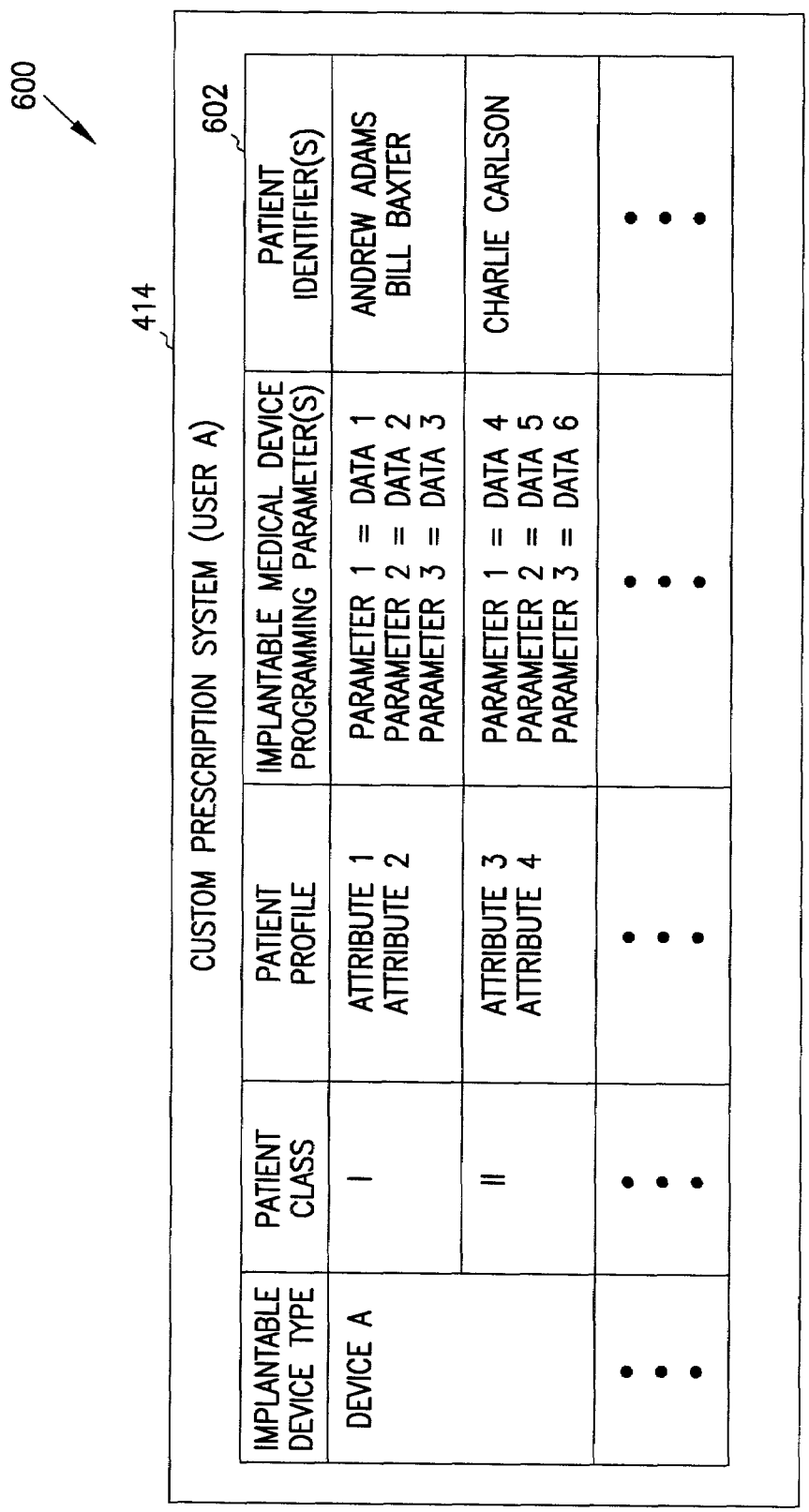
FIG. 6 is a block diagram representing a custom prescription system defined by a user for determining a set of parameters for use in programming an implantable medical device.

Referring to FIG. 6, a block diagram 600 represents one custom prescription system 414 hosted on central server 104, according to one embodiment of system 100. Custom prescription system 414 is an object, including code and data, defined by a user to determine a set of parameters for programming an implantable medical device. The data is illustrated using a table 602 that represents a data structure that stores information defined by the user. The first column of table 602 identifies the type of programmable medical device (e.g., "Device A"). Since the first column can have multiple entries, system 414 can be used for programming multiple types of medical devices. In another embodiment, system 414 is only used for programming one type of medical device, and the first column can be eliminated.

The second column of table 602 identifies different classes of patients who may be implanted with the implantable medical device. For example, FIG. 6 indicates that two classes of patients (i.e., Classes I and II) may be implanted with Device A. The number of classes is defined by the user, and there may be fewer than or more than two classes for each device. For each class, the third column of table 602 provides a patient profile that defines that class. The profile of each class includes one or more attributes shared by patients in that class. For example, if a patient exhibits "Attribute 1" and "Attribute 2", that patient would be classified as being of Class I. The number of attributes that make u
each patient profile is defined by the user, and each profile may include fewer than or more than two attributes.

Each attribute is typically a function of one or more of the patient characteristics that are communicated to central server 104 by programmer 106. For example, the function may include a determination of whether a particular characteristic is equal to a certain value (e.g., is the patient female?), is within a range of values (e.g., is the most recent measured intrinsic QRS width between 80 and 100 msec?), is less than a value (e.g., is the QRS width less than 80 msec?), is greater than a value (e.g., is the QRS width greater than 100 msec?), etc. The function may also include a function of two or more characteristics of the patient (e.g., is the patient female, and is the QRS width between 80 and 100 msec?). The attributes that make up a particular patient profile will be defined by the user. In one embodiment, programmer 106 and central server 104 cooperate to allow the user to create a patient profile (e.g., when the user selects this option on programmer 106), or to update an existing patient profile.

The fourth column of table 602 specifies a set of programming parameter(s) for the implantable medical device 110 being programmed for a class of patients who exhibit the patient profile for that class. For example, assume that Device A has three programming parameters designated Parameter 1, Parameter 2 and Parameter 3. For patients classified as belonging to Class I, the parameters for programming Device A are specified as Parameter 1=Data 1, Parameter 2=Data 2 and Parameter 3=Data 3. For patients classified as belonging to Class II, the parameters for programming Device A are specified as Parameter 1=Data 4, Parameter 2=Data 5 and Parameter 3=Data 6. Note that data values may be the same or different for any of the parameters (e.g., Data 1 may or may not equal Data 4).

In one embodiment, table 602 includes a fifth column for storing a patient identifier that uniquely identifies the user's patients who belong to the particular class of patients. For example, Andrew Adams and Bill Baxter have been classified as belonging to Class I for the purposes of programming Device A, while Charlie Carlson has been classified as belonging to Class II. Alternatively, another form of patient identifier (such as a patient identifier number) could be stored in this field. The patient identifier information may be used by a medical practitioner to help determine the classification of a particular patient. For example, a medical practitioner who is programming Device A for Doug Duncan and believes that Mr. Duncan's condition is similar to that of Mr. Adams may want to classify Mr. Duncan in the same class as Mr. Adams. In another embodiment, table 602 does include the fifth column.

Figure 7:
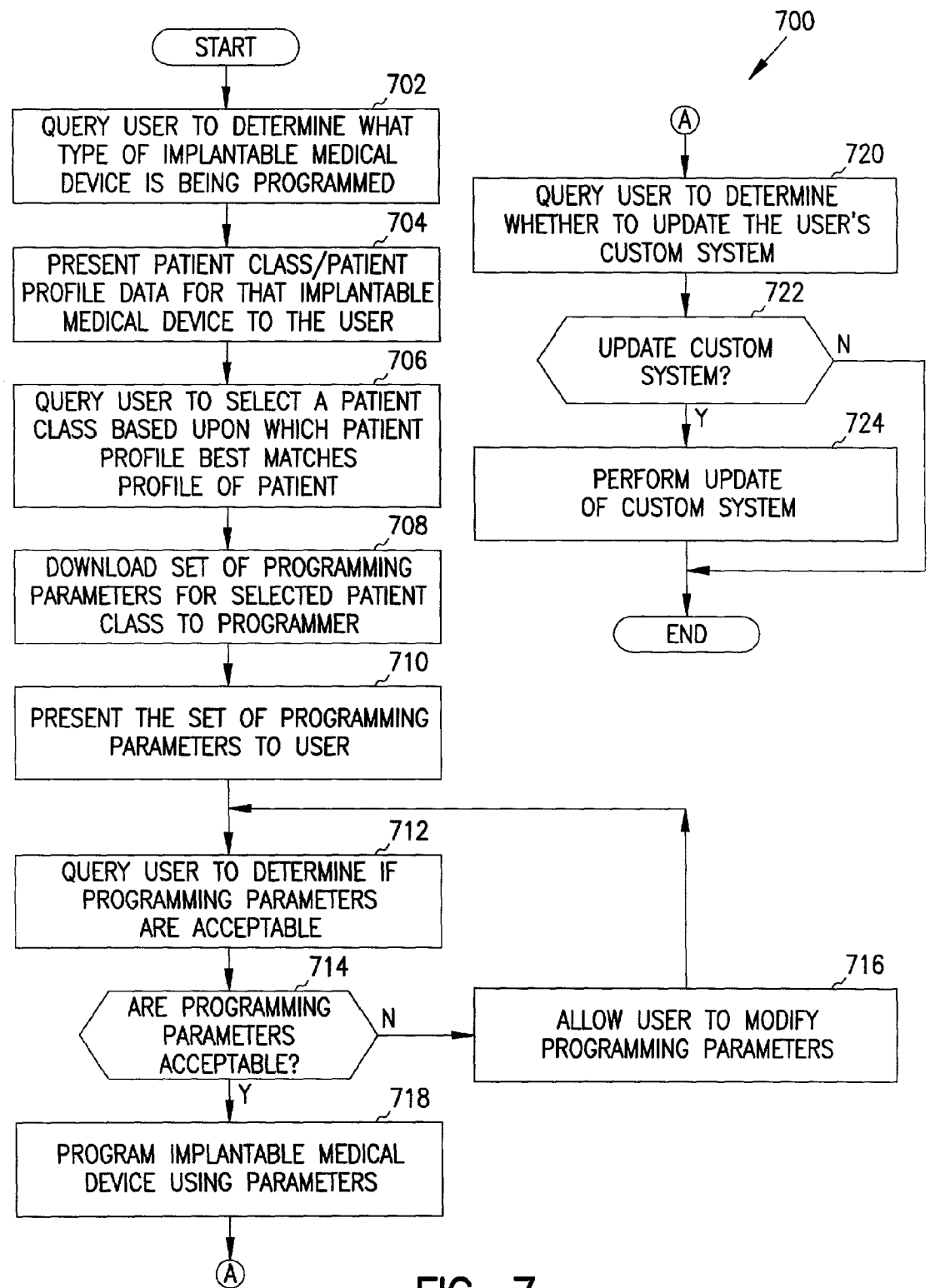
FIG. 7 is a flow chart illustrating exemplary logic for programming an implantable medical device using the custom prescription system of FIG. 6.

Referring to FIG. 7, a flow chart 700 illustrates logic by which system 100 programs an implantable medical device 110 using a custom prescription system like that of FIG. 6. This logic is performed when the user has selected his or her custom prescription system 414.

At 702, system 100 queries the user to determine what type of medical device 110 is being programmed. For example, in one embodiment, central server 104 transmits data identifying the types of medical devices specified in the first column of table 602 to programmer 106, and programmer 106 presents that data to the user on a user output device 322 and receives a signal selecting one of the device types from a user input device 320. In another embodiment, programmer 106 determines the type of medical device being programmed from a signal communicated to the programmer from the medical device. In another embodiment, system 100 only programs one type of device, and 702 is not needed.

At 704 and 706, system 100 presents patient class/patient profile information for the medical device being programmed to the user, and queries the user to select a patient class based upon which patient profile best matches the profile of the patient. For example, in one embodiment, the patient class/patient profile portion of table 602 is communicated from central server 104 to programmer 106, and programmer 106 presents that information to the user on a user output device 322 and receives a signal selecting one of the classes from a user input device 320. At 708, system 100 downloads the set of programming parameters for the selected patient class from central server 104 to programmer 106. At 710, system 100 presents that set to the user on a user output device 322. At 712 and 714, system 100 queries the user to determine if these programming parameters are acceptable. If not, system 100 allows the user to modify one or more of the parameters at 716, and then returns to 712 to determine if the parameters are acceptable. Once the parameters are acceptable, system 100 uses programmer 106 to program the implantable medical device 110 using the parameters.

At 720 and 722, system 100 queries the user to determine whether to update the user's custom prescription system. If not, the programming operation is complete. If so, system 100 updates the custom prescription system at 724. In one embodiment, system 100 allows the user to add an identifier for the current patient to the patient identifier field of the patient class that the current patient was determined as belonging to. In one embodiment, if any of the programming parameters was modified at 716, system 100 allows the user to define a new patient class that corresponds to the modified set of programming parameters. Once the custom prescription system is updated, the programming operation is complete.

The use of custom prescription systems may be particularly advantageous or convenient for medical practitioners who practice in multiple locations (e.g., at three or four different hospitals). By using system 100, such practitioners can store programming data in central server 104 where that data is always available regardless of where they are practicing.

In one embodiment, any or all of the expert prescription systems 412 is structured similarly to custom prescription systems 414, except that the person who defines and updates the expert prescription system 412 is an expert in the field. This expert can use one of expert clients 108, or can use a medical device programmer, to define or update the system 412.

Figure 8:
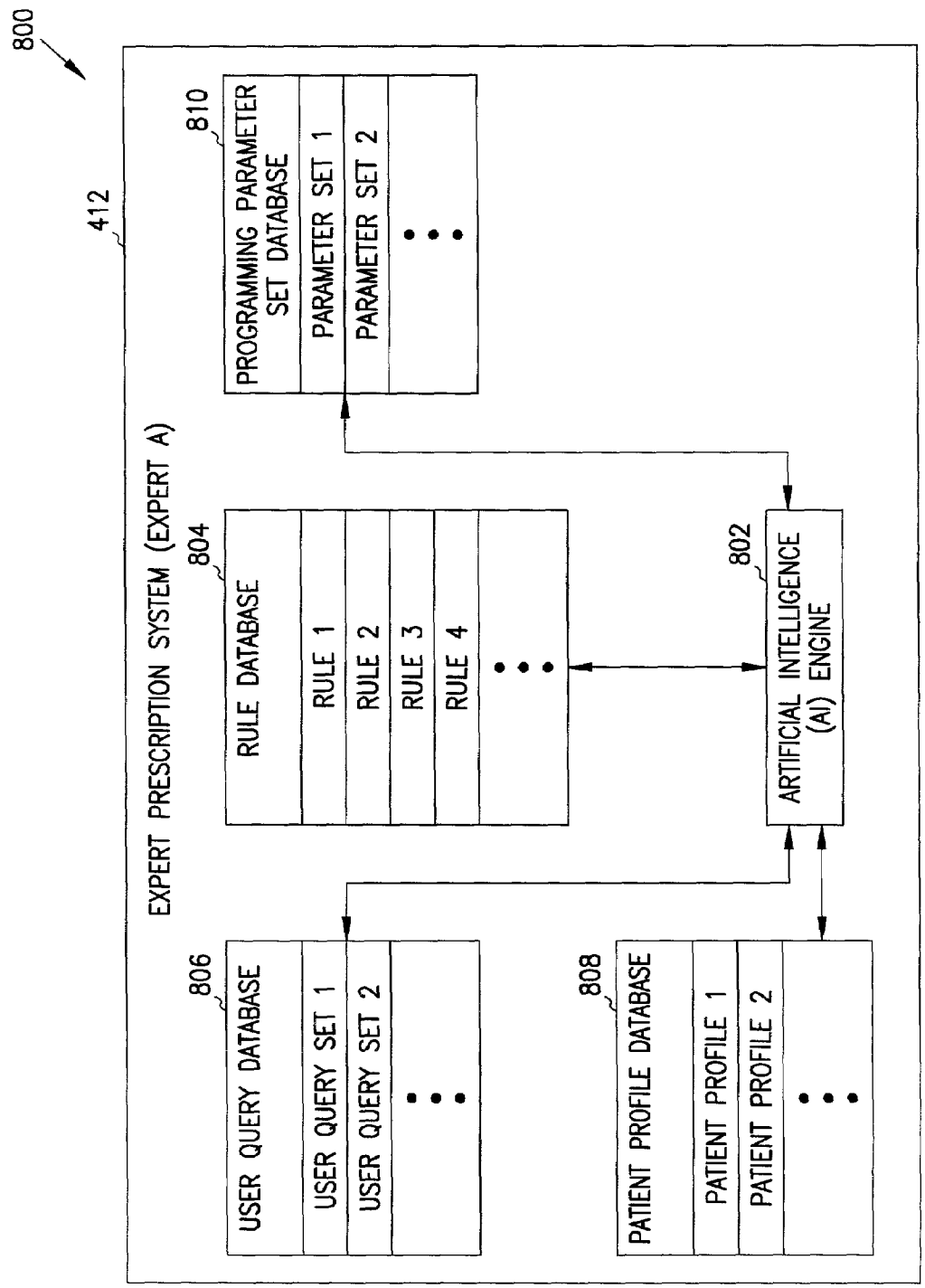
FIG. 8 is a block diagram representing an expert prescription system defined by an expert for determining a set of parameters for use in programming an implantable medical device.

In another embodiment, any or all of expert prescription systems 412 comprises an artificial intelligence (AI) engine. Referring to FIG. 8, a block diagram 800 represents an expert prescription system 412 incorporating an AI engine, according to one embodiment of system 100. System 412 is an object, including code and data, defined by an expert to determine a set of parameters for programming a medical device. System 412 includes an AI engine 802, a rule database 804, a user query database 806, a patient profile database 808, and a programming parameter set database 810. AI engine 802 is built, for example, using commercially-available expert-system software. Rule database 804 stores a number of expert system rules for use by AI engine 802. User query database 806 stores a number of user query sets. Patient profile database 808 stores a number of patient profiles, such as those in FIG. 6. Programming parameter set database 810 stores a number of programming parameter sets, such as those in FIG. 6. Expert prescription system 412 is developed by having an expert work with AI engine 802 to capture the knowledge and skills of the expert.

Figure 9:
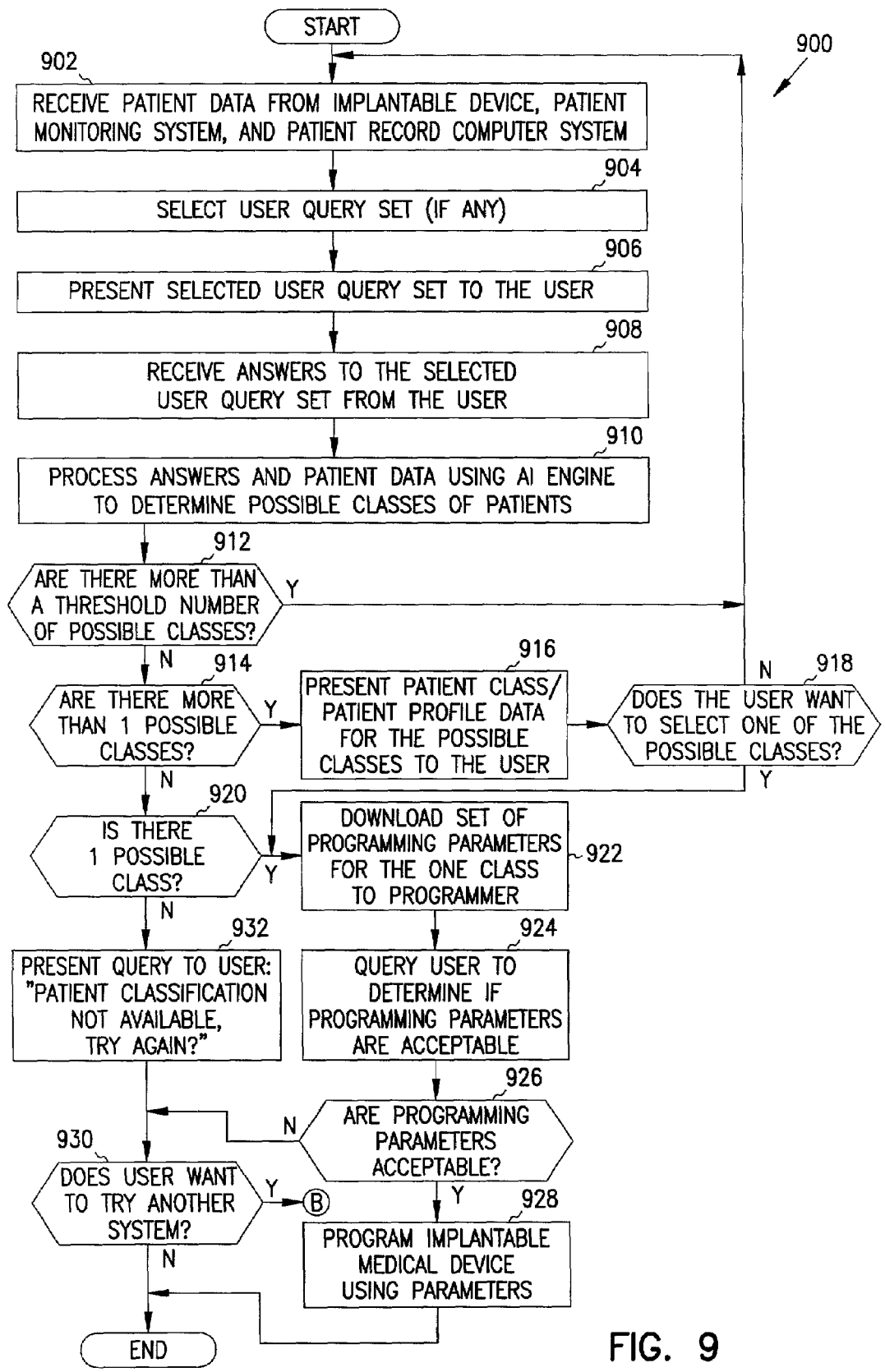
FIG. 9 is a flow chart illustrating exemplary logic for programming an implantable medical device using the expert prescription system of FIG. 8.

Referring to FIG. 9, a flow chart 900 illustrates logic for programming a medical device using the expert prescription system of FIG. 8. At 902, system 100 receives patient characteristic data from one or more sources. For example, programmer 106 receives data from one or more of the medical device being programmed, patient monitoring system 326, and patient records computer system 330. At 904, system 100 selects one of the user query sets stored in user query database 806. Each user query set includes one or more questions about the patient. On the first pass through this logic, in one embodiment, the selected user query set is a base set of one or more questions that the expert believes is generally needed to determine how to program the medical device. At 906, system 100 presents the selected user query set to the user using a user output device 322. At 908, system 100 receives answers to the selected user query set from the user using a user input device 320. At 910, system 100 processes the answers, and the patient data from 902, using AI engine 802 to determine one or more possible classes of patients to which the patient might belong.

At 912, system 100 determines whether the patient might belong to more than a threshold number of possible classes. The threshold represents a reasonable number of possible classes that could be presented to the user to select from. In one embodiment, the threshold number is four, although other threshold numbers such as two, three, five, etc. could be used. If there are more than the threshold number of possible classes, system 100 returns to 902, so that additional data can be received from any or all of medical device 110, patient monitoring system 326, patient records computer system 330, and the user. Note that the user query set selected at 904 will often contain fewer questions for the user at this stage, since the user has already answered some questions and system 100 is now trying to narrow the number of possible patient classifications. This iterative process continues until system 100 narrows the number of possible classes to less than or equal to the threshold number.

At 914, system 100 determines whether there are more than one, but no more than the threshold number, of possible classes to which the patient might belong. If so, at 916, system 100 presents patient class/patient profile data for all of the possible classes to the user to give the user the opportunity to manually select from among these classes. For example, if the threshold number is four, then the user could be presented with two, three or four possible patient profiles. At 918, system 100 determines if the user wants to select one of the possible classes. The user can input his or her decision using a user input device 320. If not, system 100 returns to 902 to gather additional information in an attempt to further narrow the number of possible classes. If so, system 100 downloads the set of programming parameters for the selected class from central server 104 to programmer 106 at 922, queries the user to determine if these parameters are acceptable at 924 and 926, and programs the implantable medical device using the programming parameters if acceptable at 928. If the parameters are not acceptable, system 100 queries the user to determine if the user wants to try another prescription system at 930 and, if so, returns to the selection logic (FIG. 5).

At 914, system 100 determines whether there is one and only one possible class to which the patient might belong. If so, system 100 performs the programming procedure of 922, 924, 926, 928, 930 described above. If, however, system 100 is unable to determine any possible classes to which the patient might belong, then the query "Patient classification not available. Try again?" is presented to the user at 932, and system 100 either allows the user to try another prescription system, or ends without programming the medical device.

In the embodiment of FIG. 9, the user is not given the option of modifying the set of programming parameters determined by the expert prescription system. This prevents the user from modifying the set in an improper manner. In another embodiment, the user is given the option of modifying the set of programming parameters determined by the expert prescription system as was discussed in relation to 716 in FIG. 7. In either case, however, the user is not given the ability of modifying the prescription system defined by the expert.

In one embodiment, the administrator of system 100 contracts with a number of experts to define the expert prescription systems, and to update the expert prescription systems at predetermined intervals. For example, a particular expert may be given an obligation to update the expert prescription system that she created every six months. This will help to insure that the expert prescription systems reflect the current state of the art. Client systems 108 allow the experts to update their prescription systems conveniently. In one embodiment, each expert prescription system includes a "valid" flag which is set to an invalid state if the expert prescription system is not updated by the expert in a timely fashion, and system 100 prevents the selection of any expert prescription system which is not valid. By enlisting experts to create and update the expert prescription systems, the knowledge and skills of the experts can be leveraged by being made available to any users of system 100.

To update an expert prescription system, an expert may, for example, use the AI engine 802 to add a new rule to rule database 804, to delete a rule from rule database 804, or to modify a rule in rule database 804. For example, an expert may learn that it is important to determine another piece of information about a patient in order to prescribe a set of programming parameters, or may learn that another set of programming parameters provides improved therapy for a particular class of patient. By working with AI engine 802, the expert can change or update the rules in rule database 804 to reflect this new knowledge.

In one embodiment, central server 104 further includes a prescription verification system that is used to help insure that the custom and/or expert prescription systems are acceptable. In one embodiment, the prescription verification system includes a set of rules, or an AI system, that is used to evaluate a prescription system. For example, one of the rules could be that a pacemaker may not be set to operate in a monitoring mode only. Generally, these rules are designed to catch major problems in the definition of the prescription systems that would be obviously incorrect to a person of skill in the art, rather than trying to catch subtle errors. In one embodiment, if the prescription verification system finds a violation of any of the rules, system 100 attempts to alert the physician (e.g., by automatically paging or sending an email to the physician). In another embodiment, system 100 does not allow the user or expert to define or update the prescription system if a rule violation is detected. In another embodiment, system 100 informs the user or expert when a rule violation is detected, and requests confirmation from the user or expert before modifying the prescription system.

CONCLUSION

The above description and the accompanying drawings are intended to be illustrative, and not restrictive. Many other embodiments will be apparent to those of ordinary skill in the art upon reviewing the above description. For example, while the above description concentrates on the programming of implantable medical devices, system 100 may be used for programming non-implantable medical devices. Also, while some of the functions of system 100 are described as being performed by a medical device programmer, the central server or an expert client, it should be understood that the distribution of the functions within system 100 can be modified as would be apparent to a person of skill in the art. Further, while this application describes particular embodiments of the custom prescription systems and expert prescription systems, it should be understood that these prescription systems can be defined in a number of different ways by the users and by the experts. For example, a user could also use an expert system to help define his or her custom prescription system. The scope of the present invention should therefore be determined with reference to the appended claims, along with the full scope of equivalents to which such claims are entitled.

What is claimed is:

1. A centralized management system for medical devices, comprising:
   a network;
   a central server coupled to the network and including at least one prescription system for prescribing at least one programmable parameter of a medical device based upon at least one characteristic of a patient; and
   a medical device programmer coupled to the network and configured to communicate at least one characteristic of a patient to the central server via the network, to receive at least one programmable parameter from the central server via the network, and to program the medical device using the at least one programmable parameter,
   wherein the central server includes a plurality of expert prescription systems, each defined by an expert to prescribe at least one parameter of a medical device based on at least one characteristic of a patient, and
   wherein at least one of the central server and medical device programmer is configured to allow a user to select one of the plurality of expert prescription systems for prescribing the at least one parameter.

2. The centralized management system of claim 1, wherein the network is a wide area network.

3. The centralized management system of claim 1, wherein the central server includes at least one custom prescription system.

4. The centralized management system of claim 1, wherein the medical device programmer includes an interface to receive signals from a patient monitoring system that represent at least one of the at least one characteristic of the patient.

5. The method of claim 1, wherein the network includes the Internet.

6. A centralized management system for medical devices, comprising:
   a network;
   a central server coupled to the network and including at least one prescription system for prescribing at least one programmable parameter of a medical device based upon at least one characteristic of a patient; and
   a medical device programmer coupled to the network and configured to communicate at least one characteristic of a patient to the central server via the network, to receive at least one programmable parameter from the central server via the network, and to program the medical device using the at least one programmable parameter
   wherein the central server includes a plurality of custom prescription systems, each defined by a user to prescribe at least one parameter of a medical device based on at least one characteristic of a patient, and
   wherein at least one of the central server and medical device programmer is configured to allow a user to use only a custom prescription system defined by that user from among the custom prescription systems.

7. The centralized management system of claim 6, wherein the central server includes at least one expert prescription system.

8. The centralized management system of claim 6, wherein the medical device programmer includes an interface to receive signals from a patient records computer system that represent at least one of the at least one characteristic of the patient.

9. The method of claim 6, wherein the network includes the Internet.

10. A centralized management system for medical devices, comprising:
    a network;
    a central server coupled to the network and including at least one prescription system for prescribing at least one programmable parameter of a medical device based upon at least one characteristic of a patient; and a medical device programmer coupled to the network and configured to communicate at least one characteristic of a patient to the central server via the network, to receive at least one programmable parameter from the central server via the network, and to program the medical device using the at least one programmable parameter, wherein the central server includes at least one expert prescription system, and at least one custom prescription system, and at least one of the central server and the medical device programmer is configured to allow a user to select one of the expert and custom prescription systems.

11. The centralized management system of claim 10, wherein the medical device programmer is configured to program an implantable medical device.

12. The centralized management system of claim 10, wherein the medical device programmer includes an interface to receive signals from at least one user input device that represent at least one of the at least one characteristic of the patient.

13. The centralized management system of claim 10, wherein the medical device programmer includes an interface to receive signals from the medical device that represent at least one of the at least one characteristic of the patient.

14. The method of claim 10, wherein the network includes the Internet.

15. A central server for use in a centralized management system for medical devices, comprising:
   a network interface for communicating with a medical device programmer over a network; and
   at least one prescription system coupled to the network interface, each configured to receive at least one characteristic of a patient from the medical device programmer via the network, to prescribe at least one programmable parameter of a medical device based on the at least one characteristic of the patient, and to transmit the at least one prescribed programmable parameter of the medical device to the medical device programmer via the network,
   wherein the at least one prescription system includes a plurality of expert prescription systems, each defined by an expert to prescribe at least one parameter of a medical device based on at least one characteristic of a patient, and
   wherein one of the plurality of expert prescription systems is selectable by a user for prescribing the at least one parameter.

16. The central server of claim 15, wherein the network interface is configured for communicating over a wide area network.

17. The central server of claim 15, wherein the at least one prescription system includes at least one custom prescription system.

18. The method of claim 15, wherein the network includes the Internet.

19. A central server for use in a centralized management system for medical devices, comprising:
   a network interface for communicating with a medical device programmer over a network; and
   at least one prescription system coupled to the network interface, each configured to receive at least one characteristic of a patient from the medical device programmer via the network, to prescribe at least one programmable parameter of a medical device based on the at least one characteristic of the patient, and to transmit the at least one prescribed programmable parameter of the medical device to the medical device programmer via the network,
   wherein the at least one prescription system includes a plurality of custom prescription systems, each defined by a user to prescribe at least one parameter of a medical device based on at least one characteristic of a patient, and
   wherein only a custom prescription system defined by a user is employable by that user from among the custom prescription systems.

20. The central server of claim 19, wherein the at least one prescription system includes at least one expert prescription system.

21. The method of claim 19, wherein the network includes the Internet.

22. A central server for use in a centralized management system for medical devices, comprising:
   a network interface for communicating with a medical device programmer over a network; and
   at least one prescription system coupled to the network interface, each configured to receive at least one characteristic of a patient from the medical device programmer via the network, to prescribe at least one programmable parameter of a medical device based on the at least one characteristic of the patient, and to transmit the at least one prescribed programmable parameter of the medical device to the medical device programmer via the network,
   wherein the at least one prescription system includes at least one expert prescription system and at least one custom prescription system, and one of the expert and custom prescription systems is selectable by a user.

23. The central server of claim 22, wherein the at least one prescription system is configured to prescribe at least one parameter of an implantable medical device.

24. The method of claim 22, wherein the network includes the Internet.

25. A medical device programmer for use in a centralized management system for medical devices, comprising:
   a network interface for communicating over a network with at least one prescription system residing on a central server;
   a medical device interface for communicating with a medical device;
   a processor coupled to the network interface and the medical device interface, and configured to communicate at least one characteristic of a patient to the central server via the network, to receive at least one prescribed programmable parameter of the medical device from the central server via the network, and to program the medical device using the at least one prescribed programmable parameter of the medical device via the medical device interface; and
   an input device interface for receiving an input signal from a user that selects one of a plurality of expert prescription systems hosted by the central server to prescribe the at least one parameter.

26. The medical device programmer of claim 25, wherein the network interface is configured for communicating with the central server over a wide area network.

27. The medical device programmer of claim 25, wherein the medical device interface is for communicating with an implantable medical device.

28. The medical device programmer of claim 25, further comprising a patient records computer system interface to receive signals from a patient records computer system that represent at least one patient characteristic for communication to the central server.

29. The method of claim 25, wherein the network includes the Internet.

30. A medical device programmer for use in a centralized management system for medical devices, comprising:
   a network interface for communicating over a network with at least one prescription system residing on a central server;
   a medical device interface for communicating with a medical device;
   a processor coupled to the network interface and the medical device interface, and configured to communicate at least one characteristic of a patient to the central server via the network, to receive at least one prescribed programmable parameter of the medical device from the central server via the network, and to program the medical device using the at least one prescribed programmable parameter of the medical device via the medical device interface; and
   an input device interface for receiving an input signal from a user that selects a user-defined custom prescription system hosted by the central server to prescribe the at least one parameter.

31. The medical device programmer of claim 30, further comprising a user input device interface to receive signals from at least one user input device that represent at least one patient characteristic for communication to the central server.

32. The medical device programmer of claim 30, wherein signals received from the medical device via the medical device interface represent at least one patient characteristic for communication to the central server.

33. The method of claim 30, wherein the network includes the Internet.

34. A medical device programmer for use in a centralized management system for medical devices, comprising:
   a network interface for communicating over a network with at least one prescription system residing on a central server;
   a medical device interface for communicating with a medical device;
   a processor coupled to the network interface and the medical device interface, and configured to communicate at least one characteristic of a patient to the central server via the network, to receive at least one prescribed programmable parameter of the medical device from the central server via the network, and to program the medical device using the at least one prescribed programmable parameter of the medical device via the medical device interface; and
   an input device interface for receiving an input signal from a user that selects one of an expert prescription system and a custom prescription system hosted by the central server.

35. The medical device programmer 34, further comprising a patient monitoring system interface to receive signals from a patient monitoring system that represent at least one patient characteristic for communication to the central server.

36. The method of claim 34, wherein the network includes the Internet.

37. A method of programming a programmable medical device comprising:
   determining at least one characteristic of a patient at a programmer;
   communicating the at least one characteristic to a central server;
   determining at least one programmable parameter for a medical device based on the at least one characteristic using a prescription system hosted by the central server;
   communicating the at least one programmable parameter to the programmer; and
   programming the medical device using the at least one programmable parameter,
   wherein the central server hosts a plurality of expert prescription systems defined by a plurality of experts, further comprising querying the user to determine which of the expert prescription systems to use.

38. The method of claim 37, wherein determining the at least one characteristic of the patient at the programmer includes receiving signals from a user input device.

39. The method of claim 37, wherein determining the at least one characteristic of the patient at the programmer includes receiving signals from the medical device.

40. The method of claim 37, wherein determining the at least one programmable parameter includes using a custom prescription system hosted by the central server.

41. A method of programming a programmable medical device comprising:
   determining at least one characteristic of a patient at a programmer;
   communicating the at least one characteristic to a central server;
   determining at least one programmable parameter for a medical device based on the at least one characteristic using a prescription system hosted by the central server;
   communicating the at least one programmable parameter to the programmer; and
   programming the medical device using the at least one programmable parameter, wherein the central server hosts a plurality of custom prescription systems, further comprising giving a user access to only a custom prescription system defined by that user from among the custom prescription systems.

42. The method of claim 41, wherein determining the at least one characteristic of the patient at the programmer includes receiving signals from a patient monitoring system.

43. The method of claim 41, wherein communicating the at least one characteristic to the central server and communicating the at least one programmable parameter to the programmer each includes communicating over a wide area network.

44. The method of claim 41, wherein the medical device is an implantable medical device.

45. A method of programming a programmable medical device comprising:
   determining at least one characteristic of a patient at a programmer;
   communicating the at least one characteristic to a central server;
   determining at least one programmable parameter for a medical device based on the at least one characteristic using a prescription system hosted by the central server;
   communicating the at least one programmable parameter to the programmer; and
   programming the medical device using the at least one programmable parameter,
   wherein the central server hosts at least one expert prescription system and at least one custom prescription system, further comprising querying the user to determine which of the hosted prescription systems to use.

46. The method of claim 45, wherein determining the at least one characteristic of the patient at the programmer includes receiving signals from a patient records system.

47. The method of claim 45, wherein determining the at least one programmable parameter includes using an expert prescription system hosted by the central server.

* * * * *